(12) United States Patent
Yoshino et al.

(10) Patent No.: US 7,846,473 B2
(45) Date of Patent: Dec. 7, 2010

(54) IRINOTECAN PREPARATION

(75) Inventors: Keisuke Yoshino, Ann Arbor, MI (US);
Shigenori Nozawa, Kanagawa (JP);
Masashi Isozaki, Kanagawa (JP); Seigo Sawada, Tokyo (JP); Ikuo Kato, Tokyo (JP); Takeshi Matsuzaki, Tokyo (JP)

(73) Assignees: Terumo Kabushiki Kaisha, Tokyo (JP); Kabushiki Kaisha Yakult Honsha, Tokyo (JP)

( * ) Notice: Subject to any disclaimer, the term of this patent is extended or adjusted under 35 U.S.C. 154(b) by 924 days.

(21) Appl. No.: 11/597,435

(22) PCT Filed: May 31, 2005

(86) PCT No.: PCT/JP2005/009953

§ 371 (c)(1),
(2), (4) Date: Feb. 8, 2007

(87) PCT Pub. No.: WO2005/117878

PCT Pub. Date: Dec. 15, 2005

(65) Prior Publication Data

US 2008/0069868 A1 Mar. 20, 2008

(30) Foreign Application Priority Data

Jun. 1, 2004 (JP) ............................. 2004-163742

(51) Int. Cl.
*A61K 9/127* (2006.01)
(52) U.S. Cl. ...................................... 424/450
(58) Field of Classification Search ............... 424/450
See application file for complete search history.

(56) References Cited

U.S. PATENT DOCUMENTS 5,192,549 A 3/1993 Barenolz et al.

(Continued)

FOREIGN PATENT DOCUMENTS

CN 1323199 11/2001

(Continued)

OTHER PUBLICATIONS

Yasuyuki Sadzuka et al., "Effect of Liposomalization on the Antitumor Activity, Side-Effects and Tissue Distribution of CPT-11", Cancer Letters, 1998, vol. 127, pp. 99-105, Elsevier Science Ireland Ltd. (cited in specification).

(Continued)

*Primary Examiner*—Gollamudi S Kishore
(74) *Attorney, Agent, or Firm*—Buchanan Ingersoll & Rooney PC

(57) ABSTRACT

Provided is an irinotecan formulation capable of supporting irinotecan and/or a salt thereof in a closed vesicle carrier at a high concentration and existing in blood for a long period of time by dramatically improved retentivity in blood compared to a conventionally known irinotecan liposome formulation. That is, an irinotecan formulation including a closed vesicle formed by a lipid membrane, in which irinotecan and/or a salt thereof is encapsulated at a concentration of at least 0.07 mol/mol (drug mol/membrane total lipid mol). There is an ion gradient between an inner aqueous phase and an outer aqueous phase in the irinotecan formulation. The closed vesicle is preferably liposome, in which only the outer surface of the liposome is preferably modified with a surface-modifying agent containing a hydrophilic polymer.

10 Claims, 21 Drawing Sheets

U.S. PATENT DOCUMENTS

| | | |
|---|---|---|
| 2002/0146450 A1 | 10/2002 | Slater et al. |
| 2006/0193902 A1* | 8/2006 | Tardi et al. .................. 424/450 |
| 2007/0110798 A1 | 5/2007 | Drummond et al. |
| 2007/0116753 A1 | 5/2007 | Hong et al. |

FOREIGN PATENT DOCUMENTS

| | | |
|---|---|---|
| EP | 1 190 706 A1 | 3/2002 |
| JP | 2001-64158 A | 3/2001 |
| JP | 2002-527466 A | 8/2002 |
| WO | WO 95/08986 A1 | 4/1995 |
| WO | WO 98/34597 A1 | 8/1998 |
| WO | WO 99/15153 A1 | 4/1999 |
| WO | WO 00/23052 | 4/2000 |
| WO | WO 01/08663 A2 | 2/2001 |
| WO | WO 03/028697 A2 | 4/2003 |
| WO | 03/041681 A2 | 5/2003 |
| WO | 2004/087104 A1 | 10/2004 |

OTHER PUBLICATIONS

English language version of Written Opinion of the International Searching Authority.

Chinese Office Action dated Nov. 28, 2008 issued in corresponding Chinese Application No. 2005800176008.

International Search Report dated Aug. 23, 2005.

Tzung-Han Chou et al., "Effect of Composition on the Stability of Liposomal Irinotecan Prepared by a pH Gradient Method," *Journal of Bioscience and Bioengineering*, 2003 (month unknown), pp. 405-408, vol. 95, No. 4, Society of Biotechnology, Japan.

Office Action dated Aug. 13, 2009 issued in corresponding Israeli Patent Application No. 179558.

Lundberg, Bo B., et al., "Biologically active camptothecin derivatives for incorporation into liposome bilayers and lipid emulsions," *Anti-Cancer Drug Design*, 1998 (month unknown), pp. 453-461, vol. 13, Oxford University Press, USA.

Office Action issued in New Zealand Patent Application No. 551748, May 7, 2009, Intellectual Property Office of New Zealand, NZ.

Search Report and Written Opinion issued in Singapore Patent Application No. 200608044-4, May 25, 2009, Intellectual Property Office of Singapore/Austrian Patent Office, Singapore/Austria.

Official Action issued in corresponding CA Patent Appln. No. 2,567,857, Apr. 30, 2008, Canadian Intellectual Property Office, CA.

* cited by examiner

US 7,846,473 B2

IRINOTECAN PREPARATION

TECHNICAL FIELD

The present invention relates to an irinotecan formulation including a closed vesicle carrier that incorporates irinotecan and/or a salt thereof at a high concentration and to a pharmaceutical composition containing the same.

BACKGROUND ART

One category of pharmaceutical products to be used for cancer treatment is a topoisomerase inhibitor, and examples thereof include camptothecin. Camptothecin is penta cyclic alkaloid, which has been extracted and isolated from *Camptotheca acuminata* (a plant of China) by Wall et al. (USA) in 1966, and it was found to have a high antineoplastic activity and a wide antineoplastic spectrum (Non-patent Document 1). A conventional cancer chemotherapy agent exerts an antineoplastic activity by topoisomerase II inhibition, while camptothecin inhibits an enzyme function of topoisomerase that plays a role in DNA replication, repair, gene recombination, and transcription by topoisomerase I inhibition.

Camptothecin has some problems in use as a drug. Among them, with respect to water insolubility, some water-soluble camptothecin analogues each improved in terms of insolubility have been proposed (see Patent Document 1, for instance). In particular, irinotecan hydrochloride (CPT-11), which is a water-soluble camptothecin derivative and has been put on the market in 1994 in Japan, is a prodrug and exerts a high antineoplastic activity, so that it was highly expected in clinical fields. After administration, irinotecan hydrochloride that is a prodrug is metabolized into SN-38 that is an active metabolite, and it exerts an antineoplastic activity.

Meanwhile, when irinotecan and a salt thereof are administered, severe side effects such as bone marrow dysfunction and gastrointestinal disturbance are caused. Therefore, use thereof is severely restricted. In addition, there is a problem that an antineoplastic activity is decreased by hydrolysis of an α-hydroxylactone ring due to the sensitivity in an aqueous environment, which is unique to camptothecin and an analogue thereof.

In order to solve the above problems and perform the optimum cancer treatment using a camptothecin analogue as the cell cycle-specific antimetabolite, it is necessary to maintain the local concentration of the drug for a long period of time. However, there is a fact that such a drug has a half-life of as short as several hours after intravenous administration or subcutaneous administration. The drug is useful as a release control agent that can be used to deliver a pharmaceutical agent having a therapeutic concentration. One approach for solving these problems, delivering a camptothecin analogue stably and effectively to a target lesion site, and exerting an antineoplastic activity in a target lesion site is to incorporate the drug into a carrier having a closed vesicle form. Some proposals on formation of a liposome formulation including camptothecins have already been made. For example, it has been reported that, when camptothecin is included in a liposome membrane, hydrolysis of an α-hydroxylactone ring is suppressed (see, for instance, Patent Document 2 and Non-patent Document 2). In addition, there has been disclosed a method of causing a liposome membrane to contain SN-38 itself, which is an active main body of irinotecan hydrochloride (Non-patent Documents 3 and 4). However, SN-38 is difficult to stabilize in a liposome membrane and disappears rapidly in blood, so that it is difficult that the concentration of SN-38 in plasma is maintained for a long time.

There has also been reported a manufacturing example based on a customary method in which irinotecan hydrochloride (a water-soluble derivative) is enclosed in a liposome by the passive loading method and is stabilized by fixing it on the membrane of lipid bilayer electrostatically (Non-patent Document 5).

Patent Document 1: JP 3-4077 B
Patent Document 2: JP 9-504517 A
Non-patent Document 1: Am. Chem. Soc., 94 (1966), 388
Non-patent Document 2: Tomas G. Burke et al., Biochemistry, 32 (1993), 5352-5364
Non-patent Document 3: W. Gao et al., J. of Chromatography B, 791 (2003), 85-92
Non-patent Document 4: Joshua Williams et al., J. of Controlled Release, 91 (2003), 167-172
Non-patent Document 5: Yasuyuki Sazuka et al., Cancer Letter 127 (1998), 99-106

DISCLOSURE OF THE INVENTION

Problems to be Solved by the Invention

The amount of irinotecan hydrochloride to be incorporated in a liposome by the above-described method of encapsulating irinotecan hydrochloride (the passive loading method) that has already been reported is about 0.05 (drug (mol)/total lipid (mol). With such a incorporated amount, the concentration of irinotecan hydrochloride in plasma and the concentration of SN-38 that is an active metabolite thereof are hardly maintained for a long time, and those amounts are not sufficient for clinical effects. Although the retentivity of irinotecan hydrochloride in blood is improved by liposome formation, the concentration of SN-38 that is an active metabolite in plasma is hardly maintained for a long time because the disappearance rate from blood is still fast.

There has not yet been reported a formulation that encloses a clinically appropriate/sufficient encapsulation amount of irinotecan (a prodrug) and/or a salt thereof in a closed vesicle and that exists in blood in a state of suppressed hydrolysis of an α-hydroxylactone ring for a long time to maintain the concentration of SN-38 that is an active metabolite in plasma in order to maintain the concentration of SN-38 that is an active metabolite of irinotecan hydrochloride in plasma for a long time.

In view of such circumstance, an object of the present invention is to provide, as a formulation having a drug encapsulation amount sufficient for clinical effects, an irinotecan formulation capable of enclosing irinotecan and/or a salt thereof in a closed vesicle in a high encapsulation efficiency of at least 0.07 (drug (mol)/total lipid (mol)) and of maintaining the concentration of SN-38 that is an active metabolite of irinotecan hydrochloride in plasma for a long time.

Means to Solve the Problems

The inventors of the present invention have made extensive studies for attaining the above-described objects. As a result, they have obtained the following findings: when the remote loading method based on an ion gradient is particularly selected as a drug encapsulation method for irinotecan and/or a salt thereof in a closed vesicle (an ion gradient is formed inside/outside the closed vesicle, and the drug is allowed to permeate through the closed vesicle membrane to introduce the drug), the drug can be encapsulated at a high concentration, which was hardly achieved with the conventional passive loading method, and the retentivity in blood is dramatically improved compared to a liposome prepared with a conventional method, with the result that the concentration of 7-Ethyl-10-hydroxy camptothecin (SN-38) (which is an active metabolite of irinotecan hydrochloride) in plasma can be kept constant for a long period of time. Moreover, they have obtained the following findings: when the remote loading method is selected, formulation stability at 37° C. and long-term formulation stability at 4° C. can be dramatically improved. Therefore, it has been confirmed that there can be acquired a formulation including a closed vesicle in which irinotecan is encapsulated in a high encapsulation efficiency of 0.07 (drug (mol)/total lipids (mol)), which is a drug encapsulation amount sufficient for a clinical effect. There has not been reported a formulation including a closed vesicle in which irinotecan and/or a salt thereof is enclosed at such a concentration and can keep the concentration of SN-38 (which is an active metabolite of irinotecan hydrochloride) in plasma for a long time. Accordingly, in order to attain the above-described objects, the present invention provides the following.

(1) An irinotecan formulation including a closed vesicle formed by a lipid membrane, in which irinotecan and/or a salt thereof is encapsulated at a concentration of at least 0.07 mol/mol (drug mol/membrane total lipid mol).

In a preferable aspect, an irinotecan formulation incorporates the drug at a concentration higher than at least 0.1 mol drug/mol lipid.

The average particle size of an irinotecan formulation of the present invention is preferable 0.02 to 250 μm.

In the present invention, irinotecan and/or a salt thereof may be encapsulated in a closed vesicle at a high concentration by, for example, the following remote loading method using an ion gradient.

(2) The irinotecan formulation according to the item (1), in which the irinotecan formulation has an ion gradient between the inner aqueous phase and outer aqueous phase of the closed vesicle. By using the above-described ion gradient, irinotecan and/or a salt thereof can be incorporated in the closed vesicle in ionization state at the concentration.

(3) The irinotecan formulation according to the item (2), in which the ion gradient is a proton concentration gradient having a pH gradient where the pH value of the inner aqueous phase is lower than a pH value of the outer aqueous phase.

(4) The irinotecan formulation according to the item (3), in which the pH gradient is formed by a concentration gradient of an ammonium ion and/or a concentration gradient of an organic compound having an amino group capable of being protonated. For example, in the case where the ammonium ion concentration in the inner aqueous phase is higher than that of the outer aqueous phase, there can be formed a pH gradient where the pH value of the inner aqueous phase is lower than the pH value of the outer aqueous phase.

(5) The irinotecan formulation according to any one of the items (1) to (4), in which the closed vesicle is a liposome formed by a membrane of lipid bilayer containing a phospholipid as a main membrane component.

In the item (5) above, preferable is an aspect in which the main membrane component is a phospholipid having a phase transition temperature of 50° C. or more.

Specific preferable examples of the phospholipid include a hydrogenated phospholipid and/or a sphingophospholipid.

(6) The liposome may further contain a lipid other than the phospholipid and/or a surface-modifying agent.

As the other lipid, cholesterol is preferable.

Preferable examples of the surface-modifying agent include a hydrophilic polymer derivative. Specific examples of the hydrophilic polymer include a polyethylene glycol having a molecular weight of 500 to 10,000 daltons, which may be introduced as a phospholipid or cholesterol derivative.

(7) The irinotecan formulation according to the item (6), in which only the outer surface of the liposome is preferably modified with a hydrophilic polymer in an aspect in which a hydrophilic polymer derivative is contained as a surface-modifying agent.

(8) An aspect in which the irinotecan formulation according to the item (6) or (7) contains a compound having a basic functional group as the surface-modifying agent is also preferable.

Particularly preferable examples of the compound having a basic functional group include 3,5-dipentadecyloxybenzamidine hydrochloride.

(9) A pharmaceutical composition, including the irinotecan formulation according to any one of the items (1) to (8).

(10) A prophylactic and/or therapeutic method of a disease, including administering a prophylactically and/or therapeutically effective amount of the irinotecan formulation according to any one of the items (1) to (8) to a host.

(11) A method of releasing an effective amount of irinotecan and/or a salt thereof in a host, including administering the irinotecan formulation according to any one of the items (1) to (8) to the host.

(12) A method of exposing an effective amount of irinotecan and/or a salt thereof to a target site, including administering the irinotecan formulation according to any one of the items (1) to (8) to the host.

Effects of the Invention

An irinotecan formulation to be provided in the present invention encapsulates irinotecan and/or a salt thereof in a encapsulated amount of at least 0.07 (drug (mol)/total lipids (mol)) and includes the drug at a high concentration sufficient for a clinical effect. As described in Examples below, an irinotecan formulation of the present invention has dramatically improved retentivity in blood compared to a conventionally known irinotecan liposome formulation, so that it can exist in blood for a long period of time. In addition, the formulation has dramatically improved formulation stability at 37° C. and long-term formulation stability at 4° C.

BEST MODE FOR CARRYING OUT THE INVENTION

Figure 1:
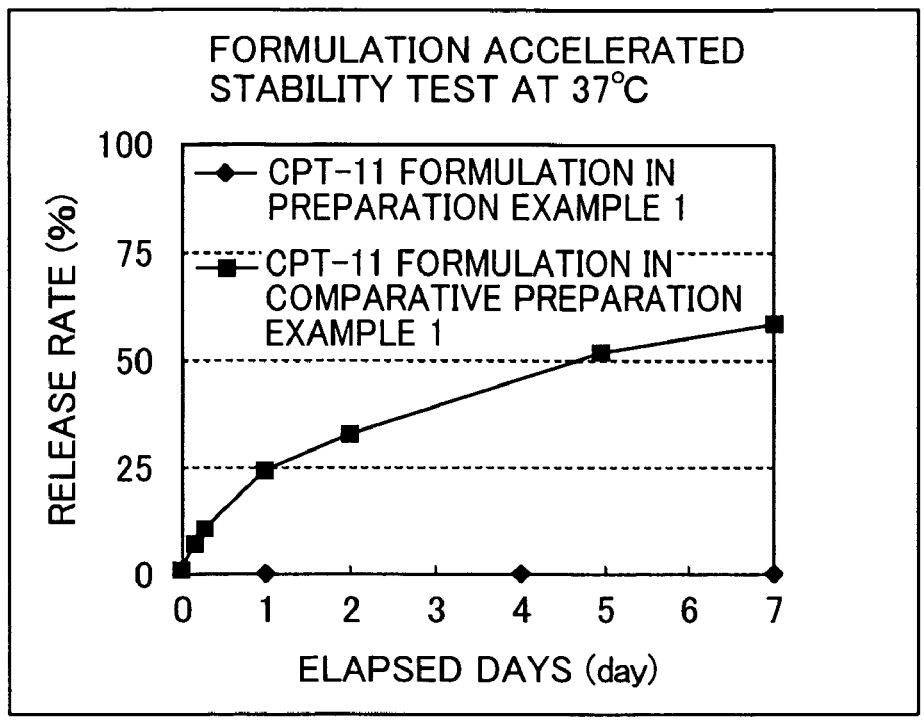
FIG. 1 This is a graph showing the results (release rate) of a formulation accelerated stability test at 37° C. for the CPT-11 formulation prepared in Example 1.

Hereinafter, the present invention will be described in more detail.

Irinotecan is a compound which has a camptothecin skeleton and is represented by a chemical name of (+)-(4S)-4,11-diethyl-4-hydroxy-9-[(4-piperidino-piperidino)carbonyloxy]-1H-pyrano[3',4':6,7]indolizino[1,2-b]quinolin-3,14 (4H,12H)-dione. Irinotecan and/or a salt thereof is an antineoplastic agent and is a water-soluble substance used as a hydrochloride salt (irinotecan•HCl (hydrochloride)) shown below. In the present specification, the term "irinotecan and/or a salt thereof" is sometimes referred to as "irinotecan" or "drug". Meanwhile, the term "irinotecan hydrochloride salt" is sometimes referred to as "irinotecan hydrochloride" or "CPT-11".

[Chemical Formula 1]

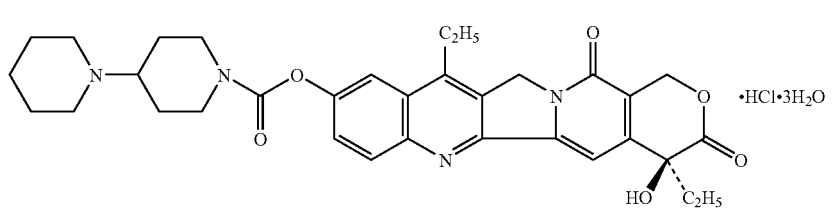

The present invention provides an irinotecan formulation that includes a closed vesicle (carrier) formed by a lipid membrane, in which the above-described irinotecan and/or a salt thereof is encapsulated in a high encapsulation efficiency of 0.07 mol/mol (drug mol/membrane total lipid mol) or more.

The closed vesicle is not particularly limited and may be in various forms as long as it has a structure capable of enclosing a drug. There may be employed a liposome, lipid microsphere, nanoparticle, or the like, which has a potential function capable of encapsulating the drug therein at a high concentration. Of those, a particularly preferable form example is the liposome.

Hereinafter, description will be made taking as an example an aspect in which a carrier of an irinotecan formulation of the present invention is a particularly preferable liposome.

A liposome is composed of a membrane of phospholipid bilayer and is a closed vesicle that has a structure forming a space separated from the outside area via the membrane that is formed based on polar characters of hydrophobic groups and hydrophilic groups of the lipid, and an aqueous phase (inner aqueous phase) was included in the vesicle space. A liposome formulation is formed using the liposome incorporating a drug as a carrier.

The "phospholipid" is a main component of a biomembrane and is an amphipathic substance, and the molecule has a hydrophobic group composed of a long-chain alkyl group and a hydrophilic group composed of a phosphate group. Examples of the phospholipid include phosphatidylcholine (=lecithin), phosphatidylglycerol, phosphatidic acid, phosphatidyl ethanolamine, phosphatidylserine, phosphatidylinositol, and a sphingophospholipid such as sphingomyelin, a natural or synthetic phospholipid such as cardiolipin or a derivative thereof, and a compound that has been hydrogenated in accordance with a conventional method. Hereinafter, the term "phospholipid" is sometimes referred to as phospholipids for encompassing those.

Of those, preferable are a hydrogenated phospholipid such as hydrogenated soybean phosphatidylcholine (HSPC), sphingomyelin (SM), and the like.

As a main membrane component, a single species of phospholipid or various species of phospholipids may be contained.

In a liposome, a phospholipid having a phase transition temperature higher than a body temperature (35 to 37° C.) is preferably used as a main membrane component so as not to easily leak an encapsulated drug during a storage period or in a body such as blood. Moreover, in the case of manufacturing such a liposome, it is sometimes exposed to a higher temperature than the body temperature. That is, the liposome is sometimes manufactured under a temperature condition of about 50 to 70° C., for example, approximately 60° C., and the heat effect on the liposome formation increases, so that a main membrane component having a phase transition temperature higher than those temperatures is particularly preferably used. Specifically, the main membrane component is preferably a phospholipid having a phase transition temperature of 50° C. or higher.

The liposome may contain other membrane component together with the above-described main membrane component. For example, it is preferable that a liposome contains a lipid other than a phospholipid or a derivative thereof (hereinafter, sometimes referred to as other lipids), and the membrane is formed of a mixed lipid together with the above-described phospholipid.

The term "lipid other than a phospholipid" means a lipid that has a hydrophobic group composed of a long-chain alkyl group or the like in its molecule and contains no phosphate group in its molecule. Examples thereof include, but are not particularly limited to, glyceroglycolipids, sphingoglycolipids, and sterols such as cholesterol (described below as a stabilizing agent), and a derivative thereof such as a hydrogenated product. Examples of the cholesterol derivative include sterols each having a cyclopentanohydrophenanthrene ring, and specific examples thereof include, but are not particularly limited to, cholesterol.

The mixed lipid may contain a single species or various species of the other lipids.

The release rate of the irinotecan formulation in plasma can be regulated by the amount of cholesterol. For decreasing the release rate to a low level, the formulation contains cholesterol in an amount of preferably 0 to 20 mol %, while for increasing the release rate to a high level, the formulation contains cholesterol in an amount of 30 to 50 mol %, preferably 40 to 50 mol %.

A liposome in the present invention may maintain the above-described membrane structure together with the above-described membrane-forming lipid and may contain other membrane component capable of being contained in the liposome without departing from the objects of the present invention. Examples of the other membrane component include a surface-modifying agent for providing an intended characteristic to a carrier membrane component by changing a lipid physical property. Examples of the surface-modifying agent include, but are not particularly limited to, a charged substance, a derivative of a hydrophilic polymer, a derivative of a water-soluble polysaccharide, and the like.

Examples of the charged substances include, but are not particularly limited to, a compound having a basic functional group such as an amino group, amidino group, or guanidino group; a compound having an acidic functional group; and the like.

Examples of the basic compound include DOTMA disclosed in JP 61-161246 A, DOTAP disclosed in JP 05-508626 A, transfectam disclosed in JP 02-292246 A, TMAG disclosed in JP 04-108391 A, 3,5-dipentadecyloxybenzamidine hydrochloride disclosed in WO 97/42166, and the like, salt, DOSPA, TfxTM-50, DDAB, DC-CHOL, and DMRIE.

Examples of the compound having the acidic functional group include: a fatty acid such as oleic acid, stearic acid; gangliosides having sialic acid such as ganglioside GM1 and ganglioside GM3; an acidic amino acid-based surfactant such as N-acyl-L-glutamine, and the like.

In the case that the above-described charged substance is a substance including a compound having a basic functional group binding to a lipid, it is referred to as a cationized lipid. The lipid moiety of the cationized lipid is stabilized in a lipid bilayer of a liposome, and the basic functional group moiety may exist on the membrane surface of the lipid bilayer of the carrier (on the outer membrane surface and/or on the inner membrane surface). Modification of the membrane with a cationized lipid enables enhancement of adhesiveness or the like between the liposome membrane and the cell.

Examples of water-soluble polysaccharides include, but are not particularly limited to, water-soluble polysaccharides such as glucuronic acid, sialic acid, dextran, pullulan, amylose, amylopectin, chitosan, mannan, cyclodextrin, pectin, and carrageenan. An example of a water-soluble polysaccharide derivative includes glycolipid or the like.

Examples of hydrophilic polymers include, but are not particularly limited to, polyethylene glycol, Ficoll, polyvinyl alcohol, styrene-maleic anhydride alternating copolymer, divinyl ether-maleic anhydride alternating copolymer, polyvinyl pyrrolidone, polyvinyl methyl ether, polyvinyl methyl oxazoline, polyethyl oxazoline, polyhydroxypropyl oxazoline, polyhydroxypropyl methacrylamide, polymethacrylamide, polydimethyl acrylamide, polyhydroxypropyl methacrylate, polyhydroxyethyl acrylate, hydroxymethyl cellulose, hydroxyethyl cellulose, polyasparto amide, and synthetic polyamino acid.

The hydrophilic polymer preferably has a structure for modifying a liposome. In particular, one end of the polymer chain preferably has the structure. That is, it is preferable that the hydrophilic polymer to be used for modification includes a main body moiety of the hydrophilic polymer and a structural moiety for modifying a liposome. In the case that the structure is a hydrophobic moiety such as a lipid, the main body moiety of the hydrophilic polymer is fixed so as to project from on the outside surface of the liposome in the form that the hydrophobic moiety is inserted in the liposome membrane, while in the case where the structure is a reactive functional group capable of binding covalently to a liposome membrane component, the main body moiety of the hydrophilic polymer is fixed so as to project from on the outside surface of the liposome by a covalent bond to a liposome membrane component such as a phospholipid exposed on the outside surface of the liposome.

Hereinafter, there will next be described a hydrophobic compound to be used for forming a hydrophilic polymer-hydrophobic polymer compound by a bond to a main body moiety of a hydrophilic polymer.

The hydrophobic compound is not particularly limited. Examples thereof include a compound having a hydrophobic region (hydrophobic compound). Examples of the hydrophobic compound include: a phospholipid and other lipid such as sterol that form a mixed lipid described below; a long-chain aliphatic alcohol; a glycerine fatty acid ester; and the like. Of those, a phospholipid is a preferable aspect. Further, the hydrophobic compound may have a reactive functional group. A bond formed by the reactive functional group is desirably a covalent bond, and specific examples thereof include, but are not particularly limited to, an amide bond, ester bond, ether bond, sulfide bond, or disulfide bond.

An acyl chain included in the phospholipid is desirably a saturated fatty acid. The chain length of the acyl chain is desirably $C_{14}$ to $C_{20}$, more desirably $C_{16}$ to $C_{18}$. Examples of the acyl chain include dipalmitoyl, distearoyl, and palmitoylstearoyl.

A phospholipid is not particularly limited. For example, as the phospholipid, there may be used one having a functional group capable of reacting with the hydrophilic polymer. Specific examples of such a phospholipid having a functional group capable of reacting with a hydrophilic polymer include phosphatidyl ethanolamine having amino groups, phosphatidylglycerol having hydroxy groups, and phosphatidylserine having carboxy groups. It is a preferable aspect that the above-described phosphatidyl ethanolamine is used.

A hydrophilic polymer-lipid derivative is composed of the above-described hydrophilic polymer and lipid. The combination of the above-described hydrophilic polymer and lipid is not particularly limited. Depending on the purpose, an appropriate combination may be employed. Examples thereof include a hydrophilic polymer derivative formed by binding at least one selected from a phospholipid, other lipids such as sterol, long-chain aliphatic alcohol, and glycerine fatty acid ester to at least one selected from PEG, PG, and PPG. Specific examples thereof include a polyoxypropylene alkyl, in particular, it is a preferable aspect that, in the case where the hydrophilic polymer is polyethylene glycol (PEG), a phospholipid or cholesterol is selected as a lipid. Examples of a PEG-lipid derivative formed by such a combination include a PEG-phospholipid derivative or a PEG-cholesterol derivative.

For the hydrophilic polymer-lipid derivative, a positively, negatively, or neutrally charged derivative may be selected by selecting the lipid. For example, in the case where DSPE is selected as a lipid, the lipid derivative exhibits a negative charge by the effect of phosphate groups, while in the case where cholesterol is selected as a lipid, the lipid derivative exhibits a neutral charge. The lipid may be selected depending on the purpose.

Molecular weight of PEG is not particularly limited. Generally, the molecular weight of PEG is 500 to 10,000 daltons, preferably 1,000 to 7,000 daltons, and more preferably 2,000 to 5,000 daltons.

Molecular weight of PG is not particularly limited. In general, the molecular weight of PG is 100 to 10,000 daltons, preferably 200 to 7,000 daltons, and more preferably 400 to 5,000 daltons.

Molecular weight of PPG is not particularly limited. Generally, the molecular weight of PPG is 100 to 10,000 daltons, preferably 200 to 7,000 daltons, and more preferably 1,000 to 5,000 daltons.

Of those, a preferable aspect is a PEG-phospholipid derivative. Examples of the PEG-phospholipid derivative include polyethylene glycol-distearoyl-phosphatidyl ethanolamine (PEG-DSPE). PEG-DSPE is preferable because it is a general-purpose compound and is easily available.

The above-described hydrophilic polymer may be used singly or two or more of the polymers may be used in combination.

Such a hydrophilic polymer-lipid derivative may be manufactured by a conventionally known method. Examples of a method of synthesizing a PEG-phospholipid derivative that is a example of the hydrophilic polymer-lipid derivative include a method of reacting PEG with a phospholipid having a functional group capable of reacting with PEG using a catalyst. Examples of the catalyst include cyanuric chloride, carbodiimide, acid anhydride, and glutaraldehyde. The above-described functional group is allowed to covalently bind to PEG by such a reaction, to thereby yield a PEG-phospholipid derivative.

In a liposome that has been subjected to a surface modification by using such a hydrophilic polymer-lipid derivative, when the adsorption of an opsonin protein or the like in plasma on the liposome surface is prevented, the liposome stability in blood is enhanced, capture by RES may be avoided, and the delivery ability of the drug to a tissue or cell that is a delivery target may be enhanced.

The modified ratio of a membrane lipid (total lipid) by the above-described hydrophilic polymer-lipid derivative is, as a rate to the membrane lipid, generally 0.1 to 20 mol %, preferably 0.1 to 5 mol %, more preferably 0.5 to 5 mol %.

Note that, in the present invention, the term "total lipids" means total lipids forming a membrane other than hydrophilic polymer-lipid derivative. Specifically, it includes phospholipids and other lipids (including cholesterol), further includes a surface-modifying agent in the case where the surface-modifying agent other than the hydrophilic polymer-lipid derivative is included, but does not include a phospholipid such as phosphatidyl ethanolamine (PE) or cholesterol that are included in the hydrophilic polymer-lipid derivative.

In the present invention, liposome membrane modification by the above-described hydrophilic polymer-lipid derivative (PEG-PE) may be performed by distributing a hydrophilic polymer (PEG) in both of the inside and outside of the lipid membrane (bilayer), or by distributing selectively in the outside membrane. Specifically, in preparation of a liposome formulation described below, the liposome may be formed after mixing a liposome-forming lipid and PEG-PE uniformly (pre-introduction). The PEG-PE may be introduced after the liposome is formed by a conventional method using a mixed lipid obtained by mixing the liposome-forming lipids containing no PEG-PE (post-introduction), but particularly preferable is a liposome formed by performing selective surface modification of only the outer layer of the lipid membrane of bilayer by modifying the membrane surface with a hydrophilic polymer from the outside after forming an unmodified liposome composed of the lipid bilayer (post-introduction). In this case, when a hydrophilic polymer-lipid derivative is used as a modifying agent for introducing a hydrophilic polymer, the hydrophilic polymer moiety is maintained in a state that it projects toward the outside, and the lipid moiety, which is a hydrophobic moiety, is maintained in a stable state by entering into the lipid bilayer membrane of liposome, so that there can be formed a liposome having the outside layer surface of the lipid, bilayer on which the hydrophilic polymer binding to the lipid exists and is distributed.

After a liposome formation step, destabilization such as aggregation occurs in the liposome depending on the temperature or time. Such destabilization is different according to the liposome lipid composition, so that the temperature or time is known to be different according to the lipid composition. In order to avoid the destabilization that is different according to the lipid composition, it is desirable that a hydrophilic polymer modification step is set after the liposome formation step.

The time for adding a hydrophilic polymer in a hydrophilic polymer addition step is desirably near immediately after the liposome formation step. Specifically, the time is preferably within 180 minutes because the heat effect on membrane components or enclosed substances is small. The time is more preferably within 120 minutes, further preferably within 45 minutes, most desirably immediately after the liposome formation step. More specifically, after the liposome formation step, the liposome dispersant may be poured directly in a hydrophilic polymer solution. Meanwhile, there may be adopted a method of adding a hydrophilic polymer solution to the liposome dispersant after the liposome formation step. In addition, there may also be adopted a method of decanting the liposome dispersant and the hydrophilic polymer solution simultaneously in another container for mixing. In this case, from the viewpoint of the concentration uniformity and temperature uniformization, it is desirable that a step of stirring by a stirrer or the like is added.

After addition of a hydrophilic polymer in a hydrophilic polymer modification step, the mixture is desirably stirred with heating for a predetermined time at a phase transition temperature or higher. The time for stirring with heating is 0 to 120 minutes, preferably 0 to 60 minutes, more preferably 0 to 45 minutes.

Contrary to the above-described methods, a liposome containing a membrane-forming lipid such as a phospholipid having a reactive functional group is manufactured by a conventional method, and then either end-activated PEG is added to the external liquid of the liposome to bind to a membrane-forming lipid such as a phospholipid having the functional group, to thereby manufacture a liposome.

Other than the above-described methods, the above-described components are mixed, and the mixture is discharged at a high pressure by a high-pressure discharge type emulsifier, to thereby yield a liposome. This method is specifically described in "Liposome in Life Science" (Terada, Yoshimura, et al.; Springer-Verlag Tokyo (1992)), which is incorporated herein by reference.

In the above-described case, for sizing the liposome to a predetermined size, some techniques are available (edited by G. Gregoriadis "Liposome Technology Liposome Preparation and Related Techniques" $2^{nd}$ edition, Vol. I-III, CRC Press), which is incorporated herein by reference.

As a lipid membrane structure of a liposome, there are known membrane structures such as a unilamellar vesicle (small unilamellar vesicle (SUV) or large unilamellar vesicle (LUV)) of lipid bilayer, and a multilamellar vesicle (MLV) including plural of lipid bilayers.

Although a liposome according to the present invention may be composed of any membrane structure, preferable is a liposome composed of a unilamellar vesicle, and specifically, LUV liposome is preferable.

A liposome dispersant may be formed into a unilamellar form by passing forcibly through a filter plural times using an extruder. In general, used are two or more species of filters having different pore sizes (a filter having a pore size larger than a predetermined pore size and a filter for obtaining a predetermined pore size finally). The more passing times of filters having different pore sizes using an extruder, the higher the rate of unilamellar formation, so that the resultant product becomes regarded as a liposome practically composed of a unilamellar vesicle. The liposome practically composed of a unilamellar vesicle specifically means a liposome having the unilamellar vesicle so that the rate of the unilamellar vesicle to all carriers (vesicles) forming a liposome formulation may be 50% or more, preferably 80% or more.

In the above-described liposome, hydrophilic polymer chains on its outer surface are distributed toward the outside of the liposome, while the inner aqueous phase-side surface of the inner layer of the lipid bilayer is not modified, so that the hydrophilic polymer chains are not substantially distributed in the inner aqueous phase. In the case of a liposome having the distribution structure, membrane stability can be maintained compared to a liposome having hydrophilic polymers distributed on the both sides of the inner and outer membranes of the bilayer membrane even if the pH value of the inner aqueous phase is low. In addition, the effect of stability in blood can be obtained even if the total amount of hydrophilic polymers are small compared to a liposome having the polymers distributed on the both sides of the inner and outer layers of the bilayer membrane.

Note that the term "retentivity in blood" means a property that an enclosed drug in a carrier is present in blood. When the drug is released from the carrier, the drug disappears rapidly from blood and affects a drug-exposed site. A drug having excellent retentivity in blood can be administered at a smaller dose.

A carrier of the present invention may be in a sphere form or a similar form. The particle size (particle outer diameter) thereof is not particularly limited but is 0.02 to 250 μm, preferably 0.03 to 0.4 μm, more preferably 0.05 to 0.2 μm. The particle outer diameter is an average value of the diameter of all particles in a liposome formulation, which is determined by the dynamic light scattering method. Specifically, the determination can be performed using Zetasizer (Malven Instruments 3000HS or S ZEM 5002).

An irinotecan formulation of the present invention may further contain a pharmaceutically acceptable stabilizer and/or antioxidant depending on its administration route. Examples of the stabilizer include, but are not particularly limited to, saccharides such as glycerol and sucrose. Examples of the antioxidant include, but are not particularly limited to, ascorbic acid, uric acid, a tocopherol homologues (for example, vitamin E), and the like. There are four tocopherol isomers ($\alpha$, $\beta$, $\gamma$, and $\delta$), all of which can be used in the present invention.

The irinotecan formulation may further contain a pharmaceutically acceptable additive depending on its administration route. Examples of the additive include water, physiological saline, a pharmaceutically acceptable organic solvent, collagen, polyvinyl alcohol, polyvinyl pyrrolidone, carboxyvinyl polymer, sodium carboxymethylcellulose, sodium polyacrylate, sodium alginate, water-soluble dextran, sodium carboxymethyl starch, pectin, methylcellulose, ethylcellulose, xanthan gum, gum acacia, casein, gelatin, agar, diglycerin, propylene glycol, polyethylene glycol, petrolatum, paraffin, stearic alcohol, stearic acid, human serum albumin (HSA), mannitol, sorbitol, lactose, PBS, a biodegradable polymer, a serum-free medium, a surfactant acceptable as a pharmaceutical additive, a physiological pH buffer acceptable in a living body, or the like. An additive to be used is not limited, but it may be selected from the above-described additives depending on its dosage form appropriately or in combination with another additive.

In the present invention, an irinotecan formulation containing such additives may be provided as a pharmaceutical composition. A pharmaceutical composition of the present invention may be stored by a general method, for example, in a refrigerator at a temperature of 0 to 8° C. or at room temperature of 1 to 30° C.

In the present invention, a liposome takes a form that CPT-11 is encapsulated. It is known that an α-hydroxy lactone ring in CPT-11 is known to be hydrolyzed at a pH range higher than a neutral condition. Therefore, in the liposome of the present invention, the inner aqueous phase of the liposome is required to be maintained at an acidic pH to suppress the hydrolysis of the α-hydroxy lactone ring regardless of whether CPT-11 is taken in the lipid bilayer or in the inner aqueous phase.

A lipid is generally known to be hydrolyzed depending on the temperature or pH value. In particular, fatty acid carboxylate esters at the sn-1 and sn-2 positions are known to be easily hydrolyzed and decomposed to a lysolipid and a fatty acid (Grit et al., Chem. Phys. Lipids 64, 3-18, 1993). Such decomposed products upset the conventional lipid membrane composition, and the permeability of the lipid membrane is improved, resulting in damaging the liposome stability. Therefore, when the inner aqueous phase is kept acidic, the pH in the outer aqueous phase is desirably approximately neutral from the viewpoint of the lipid stability.

A situation where those contrary two conditions are most severely restricted is a drug introduction step. In the drug introduction step, the mixture is required to be heated to at least the phase transition temperature of the lipid membrane, which significantly promotes the lipid hydrolysis. In order to suppress the lipid hydrolysis, it is desirable that the pH in the outer aqueous phase is set to approximately neutral. However, when the pH in the outer aqueous phase is set to approximately neutral, hydrolysis of an α-hydroxy lactone ring in CPT-11 is promoted. In view of those contrary two conditions, the pH value in the outer aqueous phase in the drug introduction step is preferably 4.0 to 8.0, more preferably 4.0 to 7.0, further preferably 5.0 to 7.0.

For completing a highly incorporated irinotecan formulation of the present invention, a carrier liposome is formed, and then a method referred to as the remote loading method is performed to introduce the drug using an ion gradient inside/outside the liposome membrane. The remote loading method may be used for a common drug capable of existing at a charge state in the case where the drug is dissolved in an appropriate aqueous medium. When an ion gradient is formed inside/outside the liposome, the drug may be encapsulated by permeating the liposome membrane depending on the formed gradient.

Examples of an ion gradient formed across liposome membrane include $Na^+/K^+$ concentration gradient. A technique for adding a drug in a previously formed liposome by the remote loading method for the $Na^+/K^+$ concentration gradient is described in U.S. Pat. No. 5,077,056 (which is incorporated herein by reference), which can be performed with reference to the description.

In the present invention, preferable examples of the ion gradient include a proton concentration gradient, and there is exemplified a mode of a pH gradient formed by setting the pH value of the inside of the membrane (inner aqueous phase) lower than the pH value of the outside of the membrane (outer aqueous phase). Specifically, the pH gradient may be formed based on an ammonium ion concentration gradient and/or a concentration gradient of an organic compound having an amino group capable of being protonated.

A specific example of a method of encapsulating a drug (irinotecan or a salt thereof) in a liposome using the ammonium ion concentration gradient will be described below. Firstly, a liposome is previously formed in an aqueous buffer containing 0.1 to 0.3 M of an ammonium salt, and the outer medium is exchanged for a medium containing no ammonium ions (e.g., a sucrose solution), to thereby form an ammonium ion gradient inside/outside the liposome membrane. The inside ammonium ions are equilibrated with ammonia and protons, and ammonia permeates the lipid membrane and disperses to eliminate ammonia from the liposome inside. With the elimination of ammonia, the equilibrated portion in the liposome moves toward proton formation. As a result, protons are accumulated in the liposome, and a pH gradient is formed inside/outside the liposome. When a drug is added to a liposome dispersant having such pH gradient, the drug is incorporated in the liposome.

An ammonium salt capable of making the ammonium ion concentration gradient includes, but not particularly limited, ammonium sulfate, ammonium hydroxide, ammonium acetate, ammonium chloride, ammonium phosphate, ammonium citrate, ammonium succinate, ammonium lactobionate, ammonium carbonate, ammonium tartrate, and ammonium oxalate.

Note that a technique itself for introducing a drug in a previously formed liposome by the remote loading method for an ammonium ion concentration gradient is described in U.S. Pat. No. 5,192,549 (which is incorporated herein by reference), which can be performed with reference to the description.

Desirably, the organic compound having an amino group capable of being protonated has a low molecular weight. Specific examples thereof include, but are not limited to, methylamine, ethylamine, propylamine, diethylamine, ethylenediamine, and the like.

In the present invention, a suitable mode is that irinotecan or a salt thereof is incorporated by the remote loading method using the ammonium ion concentration gradient.

An irinotecan formulation of the present invention is formed by incorporating irinotecan or a salt thereof in the above-described carrier at a concentration higher than 0.07 mol/mol (drug mol/membrane total lipid mol), preferably higher than 0.1 mol/mol.

In the present invention, the term "enclosure" means a state where a drug is encapsulated in a carrier. The term also means a state where part of or whole of drug molecules are included in a layer of a lipid that is a component of the carrier. A carrier of the present invention is purified by a commonly used method (such as gel filtration, dialysis, membrane separation, or centrifugation), to thereby remove drugs unloaded in the carrier.

A carrier is provided after the step of removing unloaded drugs. Therefore, a drug concentration gradient may occur between the inside and outside of the carrier via a lipid bilayer. Preferably, the carrier of the present invention contains no free drugs outside the lipid bilayer after preparation of the carrier. Then, enclosed drugs in the carrier are released to the outside area. The carrier of the present invention having enclosed drugs gets to a target site, with the result that it delivers the enclosed drugs to the target site. The delivery of the drugs to the target site may be accomplished by taking incorporated drugs in the carrier in the target site or by exerting the effect of the drugs to the target site or neighborhood thereof even if the drugs are not taken in the target site.

In the present invention, the term "release" means that an enclosed drug in a carrier diffuses to the outside of a closed vesicle by passing through a lipid membrane forming the carrier or by changing part of the structure of the lipid membrane. When irinotecan hydrochloride is metabolized in plasma into SN-38 that is an active metabolite and exposed to a target site at a high concentration for a long time, a strong antineoplastic activity is exhibited, so that it is important to control the release. The release rate of an irinotecan formulation in plasma can be controlled by adjusting the cholesterol amount, and a preferable effect is expected by adjusting the cholesterol amount. The term "release rate" means a rate of a drug that exudes to the outside of a closed vesicle from a carrier encapsulated carrier components and irinotecan hydrochloride to a drug incorporated in the carrier (weight ratio or molar ratio). The phrase "release rate is low" means that the amount of a drug exuding to the outside of a closed vesicle per unit time is small.

In the present invention, the term "target site" means a specific site in which a drug encapsulated in a carrier is released and acts, and means a cell, tissue, organ or the internal organ that is specified in each site, and an interior thereof. The target site such as a cell, tissue, organ or the internal organ, and an interior thereof may be a site to be treated with a drug. When a released drug is exposed to the site, it exerts an effect. Examples of the target site include, but are not particularly limited to, a tumor.

Examples of a tumor to be treated include, but are not particularly limited to, a solid tumor. Specific examples thereof include esophageal cancer, gastric cancer, colon cancer, large bowel cancer, rectal cancer, pancreatic cancer, liver cancer, laryngeal cancer, lung cancer, prostatic cancer, bladder cancer, breast cancer, uterine cancer, and ovarian cancer. The target site is a tumor cell, tissue, organ or the internal organ, an interior thereof, and the like. Therefore, in the present invention, a disease means the above-described tumor, and a drug is expected to exert an antineoplastic effect on it.

In the present invention, the term "exposure" means that a drug released to the outside of a carrier acts on the outside area. Specifically, when a released drug comes close to and comes into contact with a target site, the drug exerts its antineoplastic effect as its action. When the drug acts on the target site, it acts topically on a cell in a cell cycle in which DNA synthesis is being performed at the target site, so that an expected effect is exerted. To exert such an effect, a balance between the release rate of a drug from a carrier and the retentivity in blood of the carrier should be maintained.

A carrier of the present invention releases irinotecan and/or a salt thereof at a preferable release rate, and the released irinotecan and/or a salt thereof is further metabolized into SN-38 that is an active metabolite. The present invention is used for exposing SN-38 to a predetermined target site for a long time. Therefore, in the present invention, in order to prevent and/or treat a disease suffered by a host, systemic or topical administration to the host (patient) may be performed parentally by administering a carrier in which an effective amount of irinotecan and/or a salt thereof is enclosed to release the effective amount of irinotecan and/or a salt thereof in the host or to expose an effective amount of SN-38 to a target site at a high concentration for a long time. Examples of the host as an administration target include mammals, preferably human beings, monkeys, mice, livestock, and the like.

Examples of a parenteral administration route to be selected include intravenous injection (i.v.) such as drip, intramuscular injection, intraperitoneal injection, and subcutaneous injection, and an administration method may appropriately be selected depending on the age or symptom of a patient. A carrier of the present invention is administered to a patient suffering from a disease at an amount sufficient to heal the symptom of the disease or to alleviate at least part of the symptom. For example, an effective dose of a drug to be encapsulated in a carrier is selected from a range of 0.01 mg to 100 mg per kg of body weight per day. However, the dose of the carrier of the present invention is not limited thereto. For the administration period, administration may be performed after disease onset, or it may be performed prophylactically to alleviate the symptom upon onset in the case where disease onset is predicted. In addition, an administration period may appropriately be selected depending on the age or symptom of a patient.

Specific examples of the administration method include administration of a pharmaceutical composition using a syringe or drip. Meanwhile, a catheter is inserted into a body (e.g., lumen or vessel) of a patient or a host to guide its edge to around a target site, and the composition may be administered through the catheter from a predetermined target site or from the vicinity of the site or a site from which blood is expected to flow toward the target site.

As described in Examples, when the release rate of a drug enclosed in a carrier of the present invention was determined, the release rate was found to be low. To calculate the release rate, the carrier of the present invention is precipitated by centrifugation, and the amount of the drug present in the supernatant and carrier is determined.

EXAMPLES

Hereinafter, the present invention will be described in more detail by way of examples, but the present invention is not limited to those examples and test examples.

Each concentration and particle size of a drug-encapsulated liposome prepared in each example were determined as follows.

Phospholipid concentration (mg/mL): a concentration of phospholipid (HSPC) in a liposome dispersion, which was determined using a kit for phospholipid determination (Phospholipid C-Test Wako, Wako Pure Chemical Industries, Ltd.).

Total lipids concentration (mol/L): a total mol concentration (mM) of a mixed lipid that is a membrane component, which is calculated from the phospholipid concentration above. The total lipids contain lipid components in a surface-modifying agent prepared as a mixed lipid but do not contain a lipid (in examples, PE (phosphatidyl ethanolamine) in PEG-PE or Chol (cholesterol) in Chol-PEG) in a PEG derivative for introducing PEG.

Drug concentration (mg/mL): the concentration was determined as follows: the formulation obtained above was diluted 40-fold with physiological saline, and 2 mL of methanol was added to 50 μL of the mixture, followed by measurement of a fluorescence intensity (excitation wavelength: 360 nm, fluorescence wavelength: 435 nm) of the mixture using a spectrofluorimeter. The concentration of enclosed irinotecan hydrochloride is represented as "drug amount (mg)/total formulation amount (mL)".

Incorporated drug amount (molar ratio of drug/total lipids): the concentration of irinotecan hydrochloride enclosed in a carrier is represented as a molar ratio of drug/total lipids, which is calculated from a ratio of the drug concentration to the lipid concentration.

Particle size (nm): 20 μL of a liposome dispersion was diluted to 3 mL with physiological saline, and an average particle size was determined by Zetasizer 3000 HS (Malvern Instruments).

The followings are abbreviated names and molecular weights of used components.

HSPC: hydrogenated soybean phosphatidylcholine (molecular weight: 790, manufactured by Lipoid, SPC3)

Chol: cholesterol (molecular weight: 386.65, Solvay)

$PEG_{5000}$-PE: polyethylene glycol (molecular weight: 5,000)-phosphatidyl ethanolamine (molecular weight: 5,938, Genzyme Corporation)

$PEG_{2000}$-PE: polyethylene glycol (molecular weight: 2,000)-phosphatidyl ethanolamine (molecular weight: 2,725, NOF Corporation)

$PEG_{1600}$-Chol: polyethylene glycol (molecular weight: 1,600)-cholesterol (molecular weight: 1,982, NOF Corporation)

CPT-11: irinotecan hydrochloride (molecular weight: 677.19)

R-DHPE: rhodamine dihexadecanoyl phosphatidyl ethanolamine (molecular weight: 1333.81, Molecular Probes, Inc.)

TRX-20: 3,5-dipentadecyloxybenzamidine hydrochloride (molecular weight: 609.41, Joko Pharmaceutical Co., Ltd.)

Example 1

In order to confirm a method capable of attaining an irinotecan hydrochloride highly encapsulated liposome formulation, drug introduction at a high concentration was attempted by the remote loading method (Preparation Example 1) or by the passive loading method (Comparative Preparation Example 1). For all irinotecan hydrochloride incorporated liposome formulations (hereinafter, abbreviated as CPT-11 formulation), PGE-PE (post-introduced) liposome was used as a carrier although introduction methods are different.

Preparation Example 1

Remote Loading Method (1) Preparation of mixed lipid: 0.422 g of hydrogenated soybean phosphatidylcholine (HSPC) and 0.176 g of cholesterol (Chol) were dissolved in 25 mL of t-butanol (Kanto Kagaku) heated to 60° C., and the mixture was cooled in ice, followed by freeze-drying, to thereby prepare a mixed lipid of HSPC:Chol=54:46 (molar ratio).

(2) Preparation of liposome: to 0.598 g of the mixed lipid prepared above was added 10 mL of a 250 mM ammonium sulfate solution, and the lipid was allowed to swell fully. Then, the mixture was stirred with a vortex mixer, and the resultant mixture was sequentially passed through a filter (pore size: 0.2 μm×5 times, 0.1 μm×10 times, Whatman) attached to an extruder (The Extruder T. 10, Lipex biomembranes Inc.) at 68° C., to thereby prepare a liposome dispersion.

(3) Introduction of PEG-PE: to the resultant liposome dispersion was added 1.21 mL (corresponding to 0.75 mol % of the total lipids amount of the mixed lipid) of a solution of polyethylene glycol 5000-phosphatidyl ethanolamine ($PEG_{5000}$-PE) in distilled water (36.74 mg/mL), and the mixture was heated at 60° C. for 30 minutes, to thereby introduce $PEG_{5000}$-PE.

Outer aqueous phase substitution was performed using a gel column that had been subjected to solvent substitution with a 10 mM histidine/10% sucrose solution (pH 6.0).

An HSPC concentration was determined using a kit for phospholipid determination. A total lipids amount (mM) was calculated from the HSPC concentration.

(4) Drug encapsulation: an irinotecan hydrochloride (CPT-11)/RO water (reverse osmosis membrane purified water) solution having a concentration of 10 mg/mL was prepared.

The irinotecan hydrochloride solution was added to the liposome dispersion in an amount of CPT-11/HSPC=0.2 (w/w) for the HSPC concentration (mg/mL) above, and the mixture was stirred at 60° C. for 60 minutes, to thereby introduce irinotecan hydrochloride. After the introduction, the sample was cooled in ice. After the encapsulation of irinotecan hydrochloride, the liposome dispersion was passed through a gel column that had been subjected to solvent substitution with a 10 mM histidine/10% sucrose solution (pH 6.5) to remove unencapsulated drugs.

The compositions and particle sizes of the CPT-11 formulations obtained above are shown in Table 1.

Highly encapsulated CPT-11 formulations of the present invention were obtained.

Comparative Preparation Example 1

Passive Loading Method

To 0.2992 g of a mixed lipid (HSPC:Chol=54:46 (molar ratio)) prepared by the same method as that in Preparation Example 1 was added 5 mL of an irinotecan hydrochloride solution (CPT-11/10% sucrose solution having a concentration of 10 mg/mL), and the lipid was allowed to swell fully. The mixture was stirred with a vortex mixer, and the resultant mixture was sequentially passed through a filter (0.2 μm×5 times, 0.1 μm×10 times) attached to an extruder at 68° C. in the same way as Preparation Example 1, to thereby prepare an irinotecan hydrochloride-encapsulated liposome.

To the liposome was added 0.61 mL (corresponding to 0.75 mol % of the total lipids amount of the mixed lipid) of $PEG_{5000}$-PE in the same way as Preparation Example 1 (3), and the mixture was heated at 60° C. for 30 minutes, to thereby introduce $PEG_{5000}$-PE. Subsequently, unencapsulated drugs were removed using a gel column that had been subjected to solvent substitution with a 10 mM histidine/10% sucrose solution (pH 6.5).

The compositions and particle sizes of the CPT-11 formulations obtained above are shown in Table 1.

The drug was introduced in the same drug amount as that in Preparation Example 1, but CPT-11 highly encapsulated formulations were not obtained by the passive loading method.

Example 2

There was investigated the initial amount required for obtaining a CPT-11 highly encapsulated formulation of the present invention in the remote loading method.

Preparation Example 2

The procedure of Preparation Example 1 was repeated except that, in the drug encapsulation described in Preparation Example 1 (4), the CPT-11/HSPC (w/w) ratio of a CPT-11/RO aqueous solution (10 mg/mL) to be added to the PGE-PE post-introduced liposome dispersion prepared in the same way as (1) to (3) is changed to 0.1, 0.2, 0.4, and 0.8, to thereby yield CPT-11 formulations. The compositions and particle sizes of the CPT-11 formulations obtained above are shown in Table 1.

As shown in Table 1, CPT-11 highly supported (encapsulated) formulations having the drug in a fully effective concentration for clinical use can be obtained by the remote loading method by increasing the initial drug amount (ratio of drug/HSPC).

TABLE 1

| Preparation Example | Initial membrane composition (molar ratio) Lipid HSPC/Chol | PEG-PE | Lipid concentration Phospholipid (HSPC) mg/mL | Total lipids mol/L | Initial drug amount CPT-11/HSPC w/w | Supported drug Drug concentration mg/mL | Drug mol/total lipid mol | Particle size nm |
|---|---|---|---|---|---|---|---|---|
| Preparation Example 1 | 54/46 | 0.75 | 12.6 | 0.03 | 0.2 | 2.41 | 0.11712 | 120.9 |
| Comparative Preparation Example 1 | | | 13.73 | 0.032 | 0.2 | 0.29 | 0.013 | 120.8 |
| Preparation Example 2 | | | | | | | | |
| -(1) | | | 11.37 | 0.027 | 0.1 | 1.32 | 0.073 | 125.2 |
| -(2) | | | 8.98 | 0.021 | 0.2 | 1.88 | 0.132 | 124.8 |
| -(3) | | | 7.08 | 0.017 | 0.4 | 2.99 | 0.266 | 123.1 |
| -(4) | | | 4.54 | 0.011 | 0.8 | 2.96 | 0.41 | 126.5 |

Test Example 1

Accelerated Stability of Formulation at 37° C.

Each CPT-11 formulation prepared in Example 1 was heated at 37° C. for a predetermined period. After the heating, the CPT-11 formulation was diluted 20-fold by adding physiological saline, and ultracentrifugation ($1 \times 10^5$ g, 2 hours, 10° C.) was performed to precipitate a CPT-11 formulation (irinotecan hydrochloride-encapsulated liposome). The amount of irinotecan hydrochloride present in the supernatant was determined to calculate the release rate (%) of irinotecan hydrochloride from the CPT-11 formulation. The results are shown in FIG. 1.

The CPT-11 formulation prepared in Comparative Preparation Example 1 was found to have the irinotecan hydrochloride-release rate of about 60% after the heating at 37° C. for 7 days, while the CPT-11 formulation prepared in Preparation Example 1 by the remote loading method was found to release few irinotecan hydrochloride even after the heating at 37° C. for 7 days. Therefore, it was clarified that encapsulation of irinotecan hydrochloride into a liposome by the remote loading method enables preparation of a CPT-11 highly supported formulation having excellent formulation stability.

Test Example 2

Formulation Stability at 37° C.

Each CPT-11 formulation prepared in Example 2 was heated at 37° C. for a predetermined period. After the heating, for the CPT-11 formulation, the release rate of irinotecan hydrochloride was determined in the same way as Test Example 1. The release rate of each CPT-11 formulation was found to be 1% or less even after the heating at 37° C. for 14 days.

Therefore, it was clarified that the release rate of the CPT-11 formulation prepared by the remote loading method is not greatly affected by the supported drug amount (ratio of drug/total lipids), and even a CPT-11 extremely highly encapsulated formulation has excellent formulation stability.

Example 3

A liposome having a membrane composition different from that in Preparation Example 1 was used as a carrier to prepare a CPT-11 formulation. Specifically, the procedure for encapsulation of irinotecan hydrochloride was performed by the remote loading method in the same way as Preparation Example 1 using a PEG-PE post-introduced liposome (Preparation Example 3) or a PEG-PE pre-introduced liposome (Referential Preparation Example 1) including the mixed lipid shown below as a membrane component.

Preparation Example 3

(1) Preparation of mixed lipid: 1.5317 g of hydrogenated soybean phosphatidylcholine (HSPC), 0.6419 g of cholesterol (Chol), and 0.005 g of rhodamine dihexadecanoyl phosphatidyl ethanolamine (R-DHPE) were dissolved in 50 mL of t-butanol heated at 60° C., and the mixture was cooled in ice, followed by freeze-drying, to thereby prepare a mixed lipid having a molar ratio of HSPC:Chol:R-DHPE=54:46:0.1.

(2) Preparation of liposome: addition of 10 mL of a 250 mM ammonium sulfate solution, stirring with a vortex mixer, and filtering with a filter attached to an extruder (0.2 μm×5 times, 0.1 μm×10 times) were performed in the same way as Preparation Example 1 except that 0.37 g of the mixed lipid prepared above was used, to thereby yield a liposome dispersion.

Subsequently, outer aqueous phase substitution was performed with a 10 mM histidine/10% sucrose solution (pH 6.0).

(3) Introduction of PEG-PE: to the resultant liposome dispersion was added a solution of polyethylene glycol 2000-phosphatidyl ethanolamine ($PEG_{2000}$-PE) in distilled water (36.74 mg/mL) (corresponding to 2.8 mol % of the total lipids amount), and the mixture was heated at 60° C. for 30 minutes, to thereby introduce $PEG_{2000}$-PE.

(4) In the same way as the drug encapsulation in Preparation Example 1, 10 mg/mL of a CPT-11/RO water solution was added to the liposome dispersion in an amount required for CPT-11/HSPC=0.2 (w/w) to introduce irinotecan hydrochloride. Subsequently, the mixture was cooled in ice, and unencapsulated drugs were removed with a 10 mM histidine/10% sucrose solution (pH 6.5). The resultant CPT-11 formulation is shown in Table 2.

Referential Preparation Example 1

The procedure in Preparation Example 3 was repeated except that $PEG_{2000}$-PE to be added in Preparation Example 3 (3) had previously been added to the mixed lipid as a membrane component to prepare a liposome having PEG-PE dispersed in both sides of inner and outer membranes, to thereby prepare a CPT-11 formulation. The procedure is shown below.

To 0.37 g of the mixed lipid (HSPC:Chol:R-DHPE=54:46:0.1 (molar ratio)) prepared in the same way as Preparation Example 3 (1) and 0.094 g (corresponding to an amount (5.6 mol %) twice the amount in Preparation Example 3) of $PEG_{2000}$-PE was added 1 mL of ethanol, and the mixture was dissolved completely by stirring at 65° C. for 30 minutes.

After confirming that the mixture was dissolved completely by stirring, to the ethanol solution were added 10 mL of an ammonium sulfate solution prepared so as to be 250 mM. Thereafter, the same procedures as Preparation Example 3 (2) with a vortex mixer and extruder were performed, and outer aqueous phase substitution was performed for the liposome dispersion obtained by using a 10% sucrose solution.

In the same way as Preparation Example 3 (4), 10 mg/mL of a CPT-11/RO water solution was added to the liposome dispersion in an amount required for CPT-11/HSPC value=0.2 (w/w) to introduce irinotecan hydrochloride. After the introduction, the mixture was cooled in ice, and unencapsulated drugs were removed in the same way as Preparation Example 3 (4). The resultant CPT-11 formulation is shown in Table 2.

the liposome in the heated dispersion was measured every 1 week. The results are shown in FIG. 3.

Figure 2:
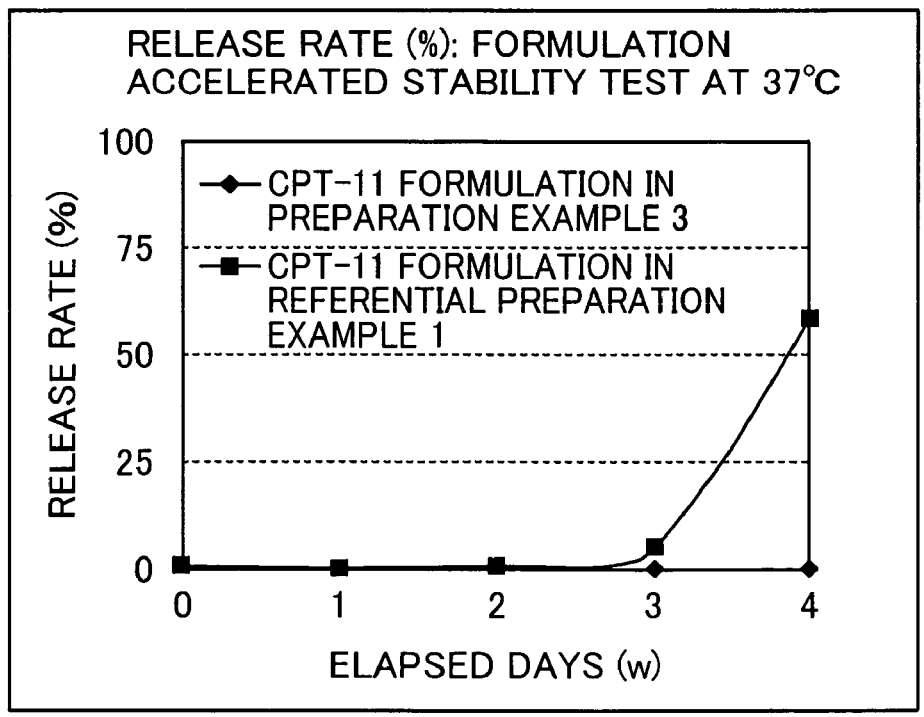
FIG. 2 This is a graph showing the results (release rate) of a formulation accelerated stability test at 37° for the CPT-11 formulation prepared in Example 3.
Figure 3:
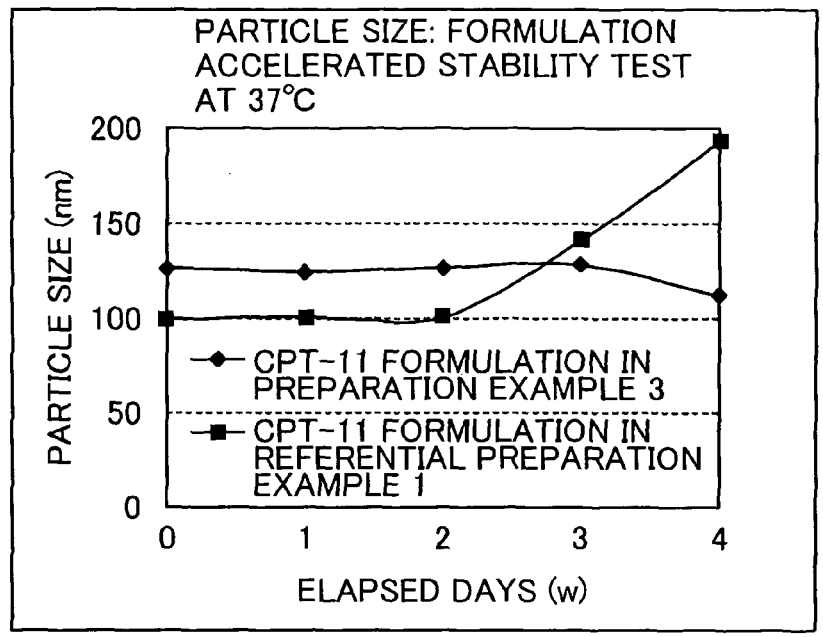
FIG. 3 This is a graph showing the results (particle size) of a formulation accelerated stability test at 37° for the CPT-11 formulation prepared in Example 3.

FIGS. 2 and 3 reveal that the liposome prepared in Preparation Example 3 released no drug at 37° C. even after 1 month (FIG. 2) and had a substantially constant particle size (FIG. 3), so that it had excellent formulation stability. On the other hand, for the PEG-PE pre-introduced liposome prepared in Referential Preparation Example 1, the drug release at 37° C. was started on the third week, the release rate on the fourth week was extremely high (FIG. 2), and the particle size increased since the third week (FIG. 3), so that it was suggested that membrane breaking occurred since the third week.

From those results, for a CPT-11 highly supported formulation of the present invention, the PEG-PE post-introduced liposome prepared by adding PEG-PE after the liposome formation was found to have a preferable form.

Example 4

In order to test long-term preservation stability and stability in blood of a CPT-11 formulation of the present invention, CPT-11 formulations were prepared by methods in Preparation Examples 4 and 5 below.

Preparation Example 4

A drug was introduced by the remote loading method in the same way as Preparation Example 1 except that outer aqueous phase substitution for the PEG-PE post-introduced liposome dispersion was performed using a gel column that had been subjected to solvent substitution with a 10 mM MES/10% sucrose solution (pH 6.0) in Preparation Example 1 (3), to thereby prepare a CPT-11 highly supported formulation. The compositions are shown in Table 3.

TABLE 2

| | Initial membrane composition (molar ratio) | | Lipid concentration | | | Supported drug | |
|---|---|---|---|---|---|---|---|
| | Lipid HSPC:Chol:R-DHPE | PEG-PE | Phospholipid mg/mL | Total lipids mol/L | Drug concentration mg/mL | Drug amount Drug mol/total lipid mol | Particle size nm |
| Preparation Example 3 | 54:46:0.1 | 2.8 | 8.12 | 0.019 | 1.52 | 0.114 | 123.8 |
| Referential Preparation Example 1 | 54:46:0.1 | 5.6 | 6.88 | 0.016 | 1.21 | 0.107 | 102.3 |

Test Example 3

Accelerated Stability of Formulation at 37° C.

For each CPT-11 formulation prepared in Example 3, an accelerated test was performed by heating it at 37° C. for 1 month. An aliquot of the heated CPT-11 formulation was collected every 1 week, and it was diluted 20-fold by adding physiological saline, followed by ultracentrifugation ($1 \times 10^5$ g, 2 hours, 10° C.) to precipitate a CPT-11 formulation. The fluorescence intensity corresponding to the amount of irinotecan hydrochloride present in the supernatant was determined to calculate the release rate from the liposome (%). The results are shown in FIG. 2. Meanwhile, the particle size of Preparation Example 5

The procedure in Preparation Example 4 was repeated except that the mixed lipid prepared in (1) below was used as a membrane component, to thereby prepare a CPT-11 highly supported formulation containing 3,5-dipentadecyloxybenzamidine hydrochloride that is a charged substance. The procedure is shown below.

(1) Preparation of mixed lipid: 0.4561 g of hydrogenated soybean phosphatidylcholine (HSPC), 0.1876 g of cholesterol (Chol), and 0.0563 g of 3,5-dipentadecyloxybenzamidine hydrochloride (TRX-20) were dissolved in 25 mL of t-butanol heated at 60° C., and the mixture was cooled in ice, followed by freeze-drying, to thereby prepare a mixed lipid of HSPC:Chol:TRX-20=50:42:8 (molar ratio).

The procedure in Preparation Example 1 (2) was repeated except that 0.700 g of the mixed lipid prepared above was used, to thereby prepare a liposome dispersion.

To the liposome dispersion was added 1.42 mL (corresponding to 0.75 mol % of the total lipids amount of the mixed lipid) of a solution of $PEG_{5000}$-PE in distilled water (36.74 mg/mL) to introduce $PEG_{5000}$-PE. Subsequently, the drug was introduced by the remote loading method in the same way as Preparation Example 1 (3) except that outer aqueous phase substitution for the liposome dispersion was performed with a 10 mM MES/10% sucrose solution (pH 6.0), to thereby prepare a CPT-11 highly supported formulation. The composition is shown in Table 3.

Test Example 4

Long-Term Preservation Stability Test at 4° C.

Each of the CPT-11 formulations obtained above was stored at 4° C. for a predetermined period. After the elapse of the predetermined period, the particle size of the CPT-11 formulation and the release rate (%) of irinotecan hydrochloride from the CPT-11 formulation were measured in the same way as Test Example 1. The results are shown in Table 3.

TABLE 3

|  |  | Preparation Example 4 | Preparation Example 5 |
|---|---|---|---|
| Initial membrane composition | Lipid | HSPC/Chol 54/46 | HSPC/Chol/TRX-20 50/42/8 |
| Molar ratio | PEG-PE | 0.75 | 0.75 |
| Lipid concentration | Phospholipid (HSPC) mg/mL | 12.02 | 11.77 |
|  | Total lipid mol/L | 0.028 | 0.03 |
| Drug concentration | mg/mL | 2.67 | 2.41 |
| Supported drug amount | mol drug/mol total lipid | 0.136 | 0.119 |
| Particle size nm | Initial | 126.3 | 123.3 |
|  | After 6-months storage | 122.2 | 125.4 |
| Release rate % | Initial | 0.63 | 0.12 |
|  | After 6-months storage | 0.38 | 0.17 |

For each of the CPT-11 formulations prepared in Example 4 above, the particle size and release rate were not changed in even after 6-months storage at 4° C. Therefore, it was clarified that each CPT-11 formulation prepared by the remote loading method has excellent long-term preservation stability.

Test Example 5

Retentivity in Blood

Each CPT-11 formulation prepared in Example 4 (Preparation Examples 4 and 5) or a solution of irinotecan hydrochloride in physiological saline (containing 1 mg/mL of irinotecan hydrochloride) was intravenously injected to the tail of a mouse (BALB/c, female, 5-week old, CLEA Japan, Inc.) in an irinotecan hydrochloride amount of 10 mg/kg (corresponding to 8.77 g/kg in terms of irinotecan amount).

Figure 4:
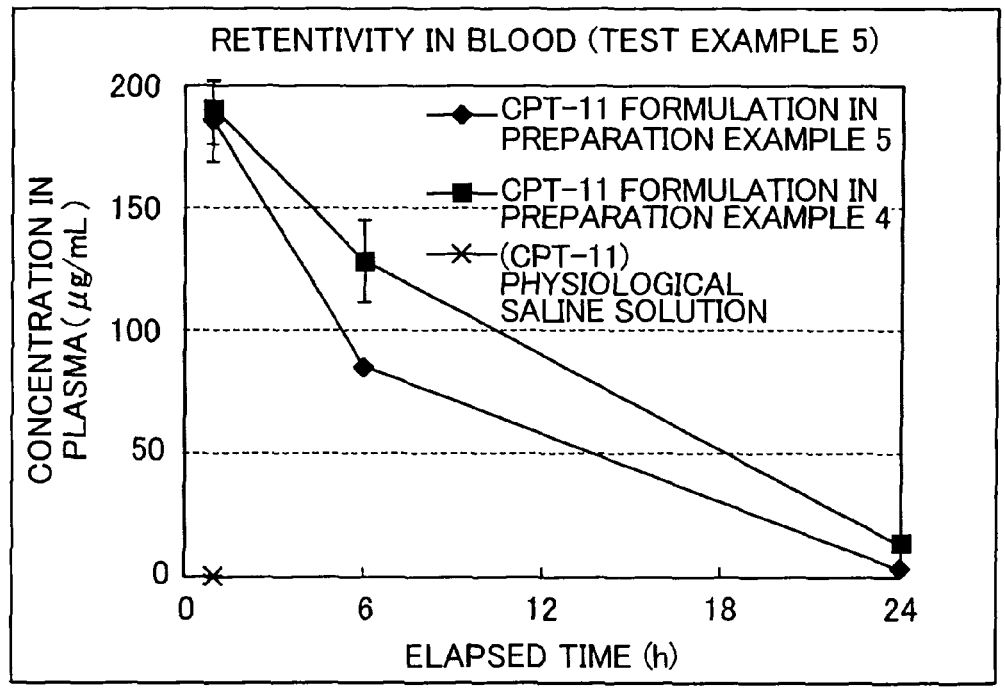
FIG. 4 This is a graph showing concentrations of irinotecan hydrochloride in plasma at each blood-drawing time after injection in a test on retentivity in blood.

Blood was drawn 1, 6, and 24 hours after the injection and centrifuged (3,000 rpm, 10 minutes, 4° C.) to collect plasma. The concentration of irinotecan hydrochloride in each plasma was measured by fluorescence intensity measurement. The plasma was stored in a refrigerator until the measurement. The results are shown in Table 4 and FIG. 4.

In the case of each CPT-11 formulation prepared in Example 4, the concentration of irinotecan hydrochloride in the plasma could be measured until 24 hours after the injection to the tail vein, while in the case of the solution of irinotecan hydrochloride in physiological saline, the concentration could be measured only 1 hour after the injection to the tail vein.

Therefore, the CPT-11 formulation prepared by the remote loading method has enabled maintaining the concentration of irinotecan hydrochloride in plasma at a high concentration for a long period of time.

TABLE 4

|  | Concentration in plasma (µg/mL) | | |
|---|---|---|---|
| Elapsed time (hr) | 1 | 6 | 24 |
| CPT-11 formulation (Preparation Example 4) | 189.41 | 128.03 | 13.18 |
| CPT-11 formulation containing TRX-20 (Preparation Example 5) | 185.29 | 84.67 | 3.38 |
| Solution of irinotecan hydrochloride in physiological saline | 0.39 | ND | ND |

Example 5

In order to test the drug efficacy of a CPT-11 highly encapsulated formulation of the present invention, CPT-11 formulations were prepared in Preparation Examples 6 to 9 below.

Preparation Example 6

The procedure in Preparation Example 4 was repeated except that the mixed lipid prepared in (1) below was used as a membrane component, to thereby prepare a CPT-11 highly supported formulation containing 3,5-dipentadecyloxybenzamidine hydrochloride that is a charged substance. The procedure is shown below.

(1) Preparation of mixed lipid: 4.562 g of hydrogenated soybean phosphatidylcholine (HSPC), 1.876 g of cholesterol (Chol), and 0.564 g of 3,5-dipentadecyloxybenzamidine hydrochloride (TRX-20) were dissolved in 50 mL of t-butanol heated at 60° C., and the mixture was cooled in ice, followed by freeze-drying, to thereby prepare a mixed lipid of HSPC:Chol:TRX-20=50:42:8 (molar ratio).

The procedure in Preparation Example 1 was repeated except that 7.002 g of the mixed lipid prepared above was used, to thereby prepare a liposome dispersion.

To the liposome dispersion was added a solution of polyethylene glycol 5000-phosphatidyl ethanolamine ($PEG_{5000}$-PE) in distilled water (36.74 mg/mL) corresponding to 0.75 mol % of the total lipids amount, and the mixture was heated at 60° C. for 30 minutes to introduce $PEG_{5000}$-PE. Subsequently, the drug was introduced by the remote loading method in the same way as Preparation Example 1 (4), to thereby prepare a CPT-11 highly encapsulated formulation. The composition is shown in Table 5.

TABLE 5

| | Initial membrane composition (molar ratio) | | Lipid concentration | | | Supported drug | | |
|---|---|---|---|---|---|---|---|---|
| | | | Phospholipid | Total lipid | Drug concentration | | Drug mol/total | Particle size |
| | Lipid HSPC:Chol:TRX-20 | PEG-PE | mg/mL | mol/L | mg/mL | amount | lipid mol | nm |
| Preparation Example 6 | 50:42:8 | 0.75 | 18.36 | 0.047 | 3.66 | | 0.115 | 134.3 |

Preparation Example 7

The procedure in Preparation Example 4 was repeated except that the mixed lipid prepared in (1) below was used as a membrane component, to thereby prepare a CPT-11 highly supported formulation containing 3,5-dipentadecyloxybenzamidine hydrochloride that is a charged substance. The procedure is shown below.

(1) Preparation of mixed lipid: 4.562 g of hydrogenated soybean phosphatidylcholine (HSPC), 1.518 g of cholesterol (Chol), and 1.126 g of 3,5-dipentadecyloxybenzamidine hydrochloride (TRX-20) were dissolved in 50 mL of t-butanol heated at 60° C., and the mixture was cooled in ice, followed by freeze-drying, to thereby prepare a mixed lipid of HSPC:Chol:TRX-20=50:34:16 (molar ratio)

The procedure in Preparation Example 1 was repeated except that 7.207 g of the mixed lipid prepared above was used, to thereby prepare a liposome dispersant.

To the liposome dispersion was added a solution of polyethylene glycol 1600-cholesterol ($PEG_{1600}$-Chol) in distilled water (36.74 mg/mL) corresponding to 2.0 mol % of the total lipids amount, and the mixture was heated at 60° C. for 30 minutes to introduce $PEG_{1600}$-Chol. Subsequently, the drug was introduced by the remote loading method in the same way as Preparation Example 1 (4) except that the outer aqueous phase substitution for the liposome dispersion was performed with a 10 mM MES/10% sucrose solution (pH 6.0), to thereby prepare a CPT-11 highly encapsulated formulation. The composition is shown in Table 6.

hydrochloride (TRX-20) were dissolved in 50 mL of t-butanol heated at 60° C., and the mixture was cooled in ice, followed by freeze-drying, to thereby prepare a mixed lipid of HSPC:Chol:TRX-20=50:42:8 (molar ratio).

The procedure in Preparation Example 1 was repeated except that 7.002 g of the mixed lipid prepared above was used, to thereby prepare a liposome dispersion.

To the liposome dispersion was added a solution of polyethylene glycol 5000-phosphatidyl ethanolamine ($PEG_{5000}$-PE) in distilled water (36.74 mg/mL) corresponding to 0.75 mol % of the total lipids amount, and the mixture was heated at 60° C. for 30 minutes to introduce $PEG_{5000}$-PE. Subsequently, the drug was introduced by the remote loading method in the same way as Preparation Example 1 (4), to thereby prepare a CPT-11 highly supported formulation. The composition is shown in Table 6.

Preparation Example 9

The procedure in Preparation Example 4 was repeated except that the mixed lipid prepared in (1) below was used as a membrane component, to thereby prepare a CPT-11 highly supported formulation. The procedure is shown below.

(1) Preparation of mixed lipid: 4.940 g of hydrogenated soybean phosphatidylcholine (HSPC) and 2.060 g of cholesterol (Chol) were dissolved in 50 mL of t-butanol heated at 60° C., and the mixture was cooled in ice, followed by freeze-drying, to thereby prepare a mixed lipid of HSPC:Chol=54:46 (molar ratio).

TABLE 6

| | Initial membrane composition (molar ratio) | | Lipid concentration | | | Supported drug | | |
|---|---|---|---|---|---|---|---|---|
| | | | Phospholipid | Total lipid | Drug concentration | | Drug mol/total | Particle size |
| | Lipid HSPC:Chol:TRX-20 | Chol-PEG | mg/mL | mol/L | mg/mL | amount | lipid mol | nm |
| Preparation Example 7 | 50:34:16 | 2 | 15.78 | 0.041 | 3.26 | | 0.119 | 133.7 |

Preparation Example 8

The procedure in Preparation Example 4 was repeated except that the mixed lipid prepared in (1) below was used as a membrane component, to thereby prepare a CPT-11 highly supported formulation containing 3,5-dipentadecyloxybenzamidine hydrochloride that is a charged substance. The procedure is shown below.

(1) Preparation of mixed lipid: 4.562 g of hydrogenated soybean phosphatidylcholine (HSPC), 1.876 g of cholesterol (Chol), and 0.564 g of 3,5-dipentadecyloxybenzamidine The procedure in Preparation Example 1 was repeated except that 7.002 g of the mixed lipid prepared above was used, to thereby prepare a liposome dispersion.

To the liposome dispersion was added a solution of polyethylene glycol 5000-phosphatidyl ethanolamine ($PEG_{5000}$-PE) in distilled water (36.74 mg/mL) corresponding to 0.75 mol % of the total lipids amount, and the mixture was heated at 60° C. for 30 minutes to introduce $PEG_{5000}$-PE. Subsequently, the drug was introduced by the remote loading method in the same way as Preparation Example 1 (4), to thereby prepare a CPT-11 highly supported formulation. The composition is shown in Table 7.

TABLE 7

| | Initial membrane composition (molar ratio) | | Lipid concentration | | Supported drug | | Particle |
|---|---|---|---|---|---|---|---|
| | Lipid HSPC:Chol:TRX-20 | PEG-PE | Phospholipid mg/mL | Total lipid mol/L | Drug concentration mg/mL | Drug mol/total lipid mol | size nm |
| Preparation Example 8 | 50:42:8 | 0.75 | 19.04 | 0.049 | 3.22 | 0.098 | 121.6 |
| Preparation Example 9 | 54:46:0 | 0.75 | 19.66 | 0.045 | 3.28 | 0.107 | 119.9 |

Example 6

The effect of the pH value of an outer aqueous phase on the drug encapsulation rate was examined.

Preparation Example 10

(1) Preparation of mixed lipid: 7.01 g of HSPC and 2.93 g of Chol were weighed, and 10 mL of absolute ethanol was added thereto. Then, those were dissolved with heating at 68° C. After confirming that those were dissolved completely, 90 mL of ammonium sulfate solution (250 mM) was added thereto, and the mixture was stirred with heating at 68° C.

(2) Preparation of liposome: after completion of the stirring with heating, the resultant mixture was passed through a filter having a pore size of 0.2 μm five times using an extruder heated to 68° C. Subsequently, the filter was exchanged for a filter having a pore size of 0.1 μm, and the filtrate was passed through the filter five times. Thereafter, the filter was exchanged for a filter having a pore size of 0.1 μm again, and the filtrate was passed through the filter five times. Introduction of $PEG_{5000}$-DSPE: after the extrusion, to the sample was added 20.4 mL of a $PEG_{5000}$-DSPE solution (36.74 mg/mL) so as to be a predetermined $PEG_{5000}$-DSPE content (mol %), and the mixture was stirred at 60° C. for 30 minutes, to thereby introduce $PEG_{5000}$-DSPE. After the introduction, the sample was cooled in ice.

(3) Outer aqueous phase substitution: for each ice-cooled sample (8 mL), outer aqueous phase substitution was performed using a gel column that had been subjected to adequate substitution with each of outer aqueous phase solutions having different pH values (pH 4.0, 5.0, 6.0, 7.0, 8.0, or 9.0), concretely, outer aqueous phase solutions having pH 4.0, 5.0 (10 mM acetic acid/10% sucrose solutions), outer aqueous phase solution having pH 6.0 (10 mM histidine/10% sucrose solution), outer aqueous phase solutions having pH 7.0, 8.0, 9.0 (10 mM Tris/10% sucrose solutions). After the outer aqueous phase substitution, each HSPC concentration was determined using a phospholipid determination kit for the liposome dispersion. The total phospholipid amount (mM) was calculated from the HSPC concentration.

(4) Drug encapsulation: there was prepared an irinotecan hydrochloride (CPT-11)/RO water (reverse osmosis membrane purified water) solution having a concentration of 10 mg/mL. The irinotecan hydrochloride solution was added to the liposome dispersion in an amount of CPT-11/total lipids amount=0.16 (mol/mol) with respect to the total lipids amount (mM) above, and the mixture was stirred at 60° C. for 60 minutes, to thereby introduce irinotecan hydrochloride. After the introduction, the sample was cooled in ice. After the encapsulation of irinotecan hydrochloride, the liposome dispersion was passed through a gel column that had been subjected to substitution with a 10 mM histidine/10% sucrose solution (pH 6.5) to remove unencapsulated drugs.

The lipid (HSPC) concentration, drug (CPT-11) concentration, and particle size of each CPT-11 formulation obtained above are shown in Table 8.

(Drug Encapsulation Efficiency)

For each CPT-11 formulation obtained above, the drug encapsulation efficiency (%) was calculated from the ratio of the final drug concentration CPT-11 with respect to the initial drug concentration 0.16 (mol/mol) according to the following expression.

Encapsulation efficiency of CPT-11(%)={Final CPT-11/Total Lipids (mol/mol)}/{Initial CPT-11/Total Lipids (mol/mol)}×100     [Mathematical Formula 1]

Figure 5:
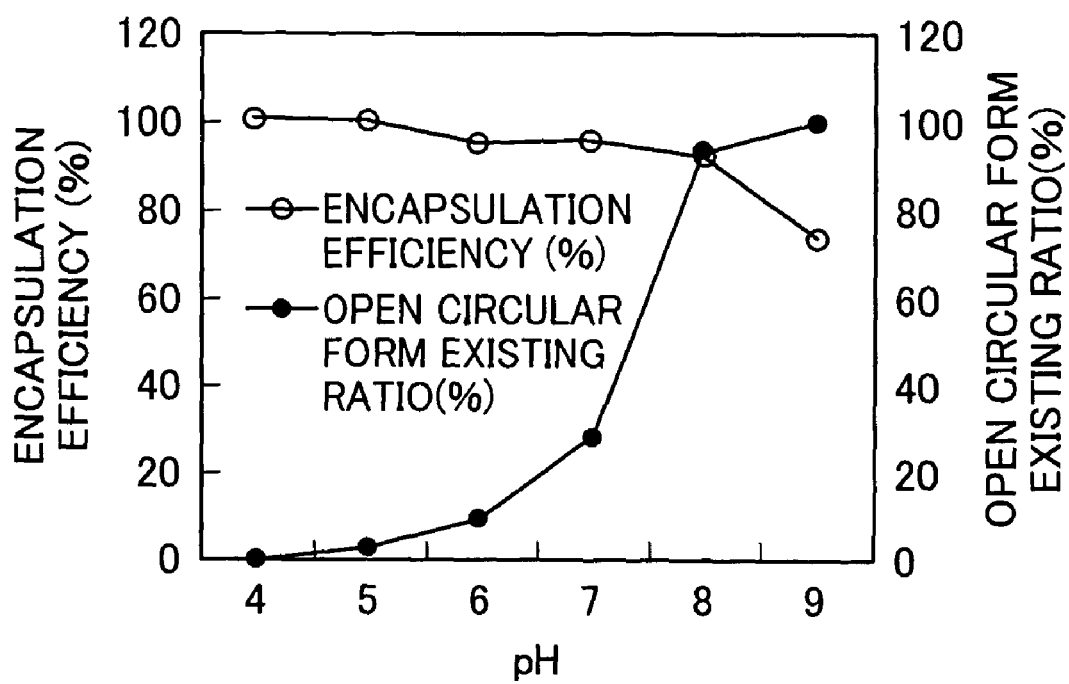
FIG. 5 This is a graph showing the relationship between the pH value of an outer aqueous phase and the CPT-11 encapsulation efficiency (%) or the open circular form existing ratio (%).

The results are shown in Table 8 and FIG. 5. The table and figure show the following: in the case where the pH value of the outer aqueous phase is 8.0 or less, the encapsulation efficiency of CPT-11(%) is a extremely high value of 90% or more, while in the case where the value is more than 8.0, the encapsulation efficiency of CPT-11(%) decreases.

TABLE 8

| Outer aqueous phase pH | HSPC concentration (mg/mL) | CPT-11 concentration (mg/mL) | Initial CPT-11/Total Lipid (mol/mol) | Final CPT-11/Total Lipid (mol/mol) | Encapsulation efficiency (%) | Particle size (nm) |
|---|---|---|---|---|---|---|
| 4 | 11.4 | 2.9 | 0.16 | 0.163 | 101.9 | 121.5 |
| | 12.5 | 3.2 | | 0.159 | 99.4 | 123.8 |
| 5 | 12.7 | 3.3 | | 0.164 | 102.5 | 122.6 |
| | 12.5 | 3.1 | | 0.157 | 98.1 | 124.0 |
| 6 | 13.0 | 3.2 | | 0.154 | 96.3 | 123.5 |
| | 14.3 | 3.4 | | 0.151 | 94.4 | 122.9 |

TABLE 8-continued

| Outer aqueous phase pH | HSPC concentration (mg/mL) | CPT-11 concentration (mg/mL) | Initial CPT-11/Total Lipid (mol/mol) | Final CPT-11/Total Lipid (mol/mol) | Encapsulation efficiency (%) | Particle size (nm) |
|---|---|---|---|---|---|---|
| 7 | 12.1 | 3.1 | | 0.158 | 98.8 | 124.7 |
|   | 13.7 | 3.2 | | 0.148 | 92.5 | 122.4 |
| 8 | 13.3 | 3.1 | | 0.147 | 91.9 | 124.1 |
|   | 13.6 | 3.2 | | 0.148 | 92.5 | 123.8 |
| 9 | 12.4 | 2.4 | | 0.120 | 75.0 | 121.4 |
|   | 12.8 | 2.3 | | 0.115 | 71.9 | 124.1 |

Example 7

The effect of the pH value of the outer aqueous phase on drug stability was examined.

To 1 mL of each of outer aqueous phases having different pH values, concretely, outer aqueous phase solutions having pH 4.0, 5.0 (10 mM acetic acid/10% sucrose solutions), outer aqueous phase solution having pH 6.0 (10 mM histidine/10% sucrose solution), outer aqueous phase solutions having pH 7.0, 8.0, 9.0 (10 mM Tris/10% sucrose solutions) (pH 4.0, 5.0, 6.0, 7.0, 8.0, or 9.0) that was used in (3) of Preparation Example 10 was added 0.7 mL of an irinotecan hydrochloride (CPT-11)/RO water (reverse osmosis membrane purified water) solution having a concentration of 10 mg/mL, and the mixture was stirred at 60° C. for 60 minutes.

The CPT-11 solution obtained above was diluted 20-fold with each outer aqueous phase solution, and 5 μL of the sample was subjected to measurement by high performance liquid chromatography. Thereafter, the hydrolysis ratio (open circular form existing ratio) (%) of α-hydroxylactone ring was calculated according to the following expression.

CPT-11 open circular form existing ratio (%)={$A_{open}$/($A_{open}$+1.102×$A_{close}$)}×100

$A_{open}$: A peak area of CPT-11 open circular form $A_{close}$: A peak area of CPT-11 close circular form The results are shown in FIG. 5.

It was clarified that, in the case where the pH value of the outer aqueous phase is 8.0 or more, the CPT-11 open circular form existing ratio (%) increased and was extremely high value of 95% or more. In order to maintain the CPT-11 activity, the pH value is required to be 4.0 or less for suppressing hydrolysis of α-hydroxylactone ring. However, from the aspect of lipid stability (lipid hydrolysis), the pH value is desirably about 6.0 to 7.0. Considering the results of Example 6, the pH value of the outer aqueous phase upon drug introduction was found to be desirably about 4.0 to 7.0.

Example 8

Preparation Example 11

(1) Preparation of Liposome 70.87 g of HSPC and 29.13 g of Chol were weighed, and 100 mL of absolute ethanol was added thereto. Then, those were dissolved with heating at 68° C. After confirming that those were dissolved completely, 900 mL of ammonium sulfate solution (250 mM) was added thereto, and the mixture was stirred with heating at 68° C.

(2) Regulation of Particle Size of Liposome

Regulation of particle size of liposome: after completion of the stirring with heating, the resultant mixture was passed through a filter having a pore size of 100 nm five times using an extruder heated to 68° C.

Introduction of $PEG_{5000}$-DSPE: after the extrusion, to the sample was added 200 mL of a $PEG_{5000}$-DSPE solution (36.74 mg/mL) so as to be a predetermined $PEG_{5000}$-DSPE content (mol %), and the mixture was stirred at 60° C. for 30 minutes, to thereby introduce $PEG_{5000}$-DSPE. After the introduction, the sample was cooled in ice.

(3) Outer Aqueous Phase Substitution

For the ice-cooled sample, outer aqueous phase substitution was performed using a cross flow filtration system with an outer aqueous phase solution (10 mM histidine/10% sucrose solution) (pH 6.5). After the outer aqueous phase substitution, the HSPC concentration and the cholesterol concentration was determined using a high performance liquid chromatography. An amount of irinotecan hydrochloride that should be encapsulated was calculated from the summation of the HSPC concentration and the cholesterol concentration as the total lipid concentration.

(4) Drug Encapsulation

There was prepared an irinotecan hydrochloride (CPT-11)/RO water (reverse osmosis membrane purified water) solution having a concentration of 10 mg/mL. The irinotecan hydrochloride solution was added to the liposome dispersion in an amount of CPT-11/total lipids amount=0.16 (mol/mol) with respect to the total lipids amount (mM) above, and the mixture was stirred at 50° C. for 20 minutes, to thereby introduce irinotecan hydrochloride. After the introduction, the sample was cooled in ice.

(5) Removal of Unencapsulated Drug

After the encapsulation of irinotecan hydrochloride, to the liposome dispersion was added the outer aqueous phase solution, and removal of unencapsulated drug was performed using a cross flow filtration system.

(6) Regulation of Concentration

For the liposome dispersion after the removal of unencapsulated drugs, an amount of irinotecan hydrochloride was determined using a high performance liquid chromatography and regulated to 5.0 mg/mL of irinotecan hydrochloride concentration.

(7) Filter Sterilization

After the regulation of concentration, the liposome dispersion was filled into a vial tube through a filter sterilization using a sterilizing filter having a pore size of 0.2 μm.

The compositions and particle sizes of the CPT-11 formulations obtained above are shown in Table 9.

TABLE 9

| | Initial Membrane composition (molar ratio) | | Lipid concentration | | Supported drug | | Particle size nm |
|---|---|---|---|---|---|---|---|
| | Lipid HSPC:Chol | PEG-DSPE | Phospholipid (HSPC) mg/mL | Total lipid mM | Drug concentration mg/mL | Drug mol/total lipid mol | |
| Preparation Example 11 | 54:46 | 0.75 | 20 | 47 | 4.92 | 0.16 | 97.2 |

Test Example 6

Antitumor Effect $2.5 \times 10^6$ cells/mouse of human prostatic cancer cells (PC-3) were implanted subcutaneously in left inguinal region of the mouse (BALB/c nude, male, 6 weeks old, Charles River Japan, Inc.). After implanting tumors, a presumptive tumor volume calculated by $\frac{1}{2} \cdot ab^2$ (a represents a longitudinal diameter of a tumor and b represents a short axis diameter thereof). From the next day of a day (day 0) in which a presumptive tumor volume achieved about 40 mm³, at 3 times in all every four days (days 1, 5, and 9), a CPT-11 preparation prepared in Preparation Example 11 or a physiological saline solution of irinotecan hydrochloride was injected to a tail vein of the mouse. There were mice without injection of either agent as a control group.

A presumptive tumor volume and a body weight of a mouse were measured at Days 1, 5, 9, 12, 16, and 22.

After extracting tumors and measuring a weight thereof at Day 22, further, an inhibition rate of tumor growth I.R. (%) was calculated by the following formula.

I.R. %=(1−average tumor weight in a treatment group/average tumor weight in a control group)×100

Figure 6:
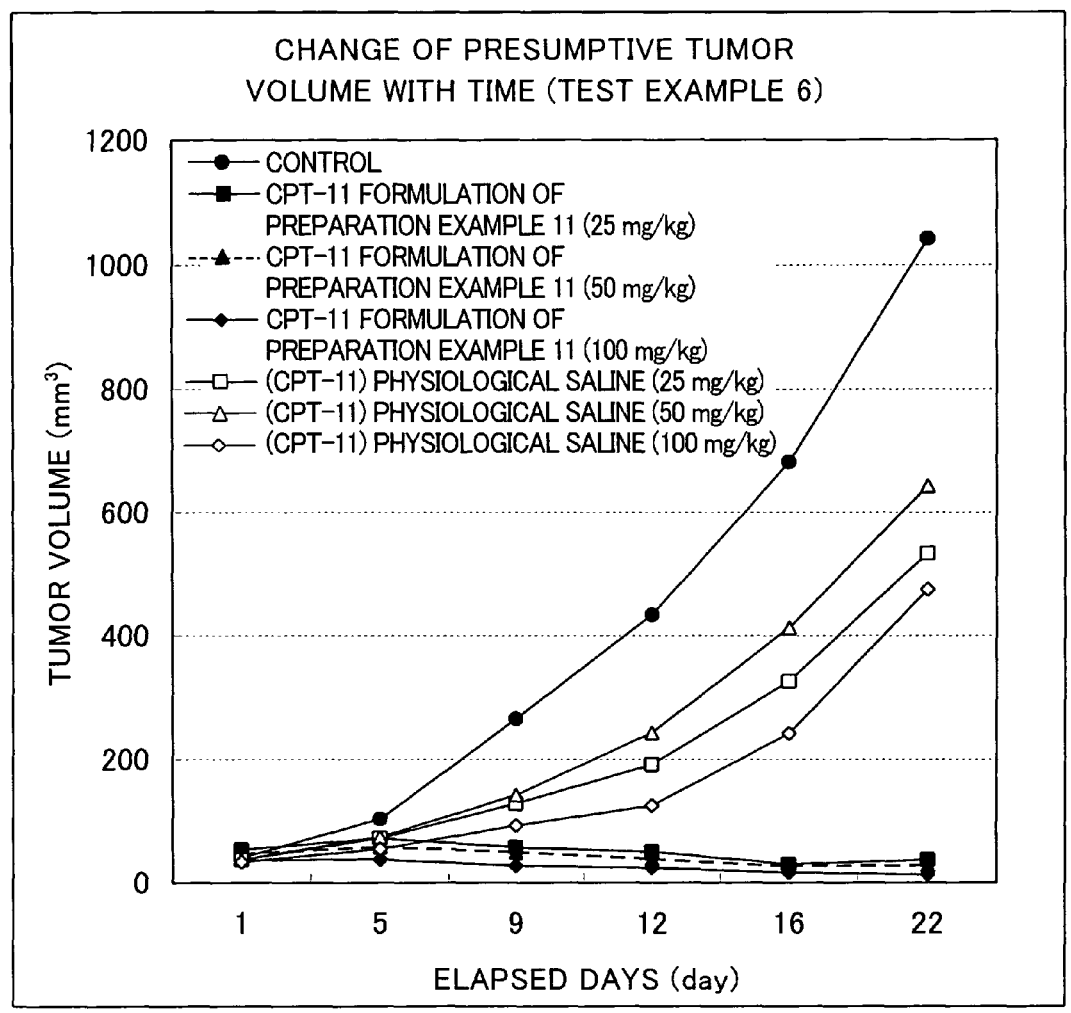
FIG. 6 This is a diagram showing antitumor effect of the CPT-11 preparation prepared in Example 8 of the present invention by change of presumptive tumor volume with time.
Figure 7:
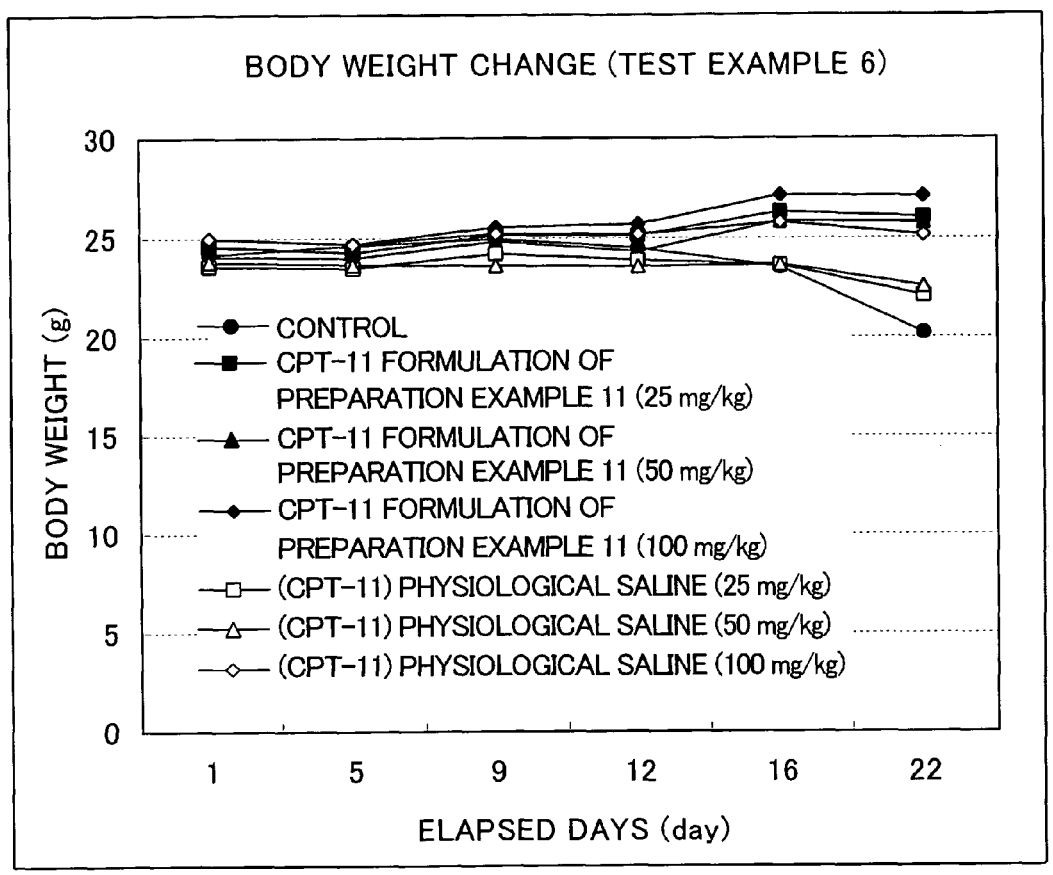
FIG. 7 This is a diagram showing antitumor effect of the CPT-11 preparation prepared in Example 8 of the present invention by change of a body weight of the mouse.

Table 10 and FIGS. 6 and 7 show the results.

The CPT-11 preparation and the physiological saline solution of irinotecan hydrochloride each proved a significant suppressive effect of tumor growth for human prostatic cancer with the treatment group compared to the control group. The CPT-11 preparation proved higher antitumor effect than that of the physiological saline solution of irinotecan hydrochloride (Table 10, FIG. 6). Further, either agent did not influence the body weight of the mouse (FIG. 7).

TABLE 10

| | Dose (mg/kg) | Tumor weight (g, mean ± S.D.) | Inhibition rate (%) |
|---|---|---|---|
| Control group | — | 1.26 ± 0.18 | — |
| CPT-11 preparation (Preparation Example 11) | 25 | 0.03 ± 0.01 | 97.9 |
| | 50 | 0.02 ± 0.00 | 98.3 |
| | 100 | 0.01 ± 0.00 | 99.0 |
| Physiological saline solution of irinotecan hydrochloride | 25 | 0.64 ± 0.25 | 49.0 |
| | 50 | 0.66 ± 0.13 | 48.0 |
| | 100 | 0.48 ± 0.20 | 62.3 |

Test Example 7

Pharmacokinetics

The CPT-11 preparation prepared in Preparation Example 11 or the physiological saline solution of irinotecan hydrochloride was continuously injected to a cephalic vein of a cynomolgus monkey (male, 4 to 5 years old, Guangxi Research Center of Primate Laboratory Animal) for 4 min until satisfying a content of irinotecan hydrochloride with 10 mg/kg.

Collecting blood from the cynomolgus monkey immediately after injection and after the beginning of injection; after 10 and 30 min; and after 1, 6, 24, 48, 72, 168, 336, and 504 hours; blood plasma was obtained by centrifugal separation. Providing 50 μL of blood plasma with 550 μL of an internal standard solution B (a methanol solution of internal standard substances) and employing centrifugal force, the supernatant was diluted with methanol 100-fold as a sample for the total CPT-11 concentration measurement. Meanwhile, Providing 50 μL of each blood plasma with 200 μL of an internal standard solution A (0.147 mol/L $H_3PO_4$ solution of internal standard substances), 200 μL thereof was subjected to a centrifugal separation (100,000×g, for 30 min, 10° C.). 100 μL in upper layer were separated and were employed solid-phase extraction, to obtain the eluent as samples for free CPT-11 (i.e., CPT-11 released from liposome, hereinafter referred as "liposome-released CPT-11") concentration measurement, SN-38 concentration measurement, and SN-38G (SN-38 10-O-glucionide) concentration measurement. The samples obtained were measured each concentration thereof with LC/MS/MS. FIGS. 8 to 11 show the results.

Figure 8:
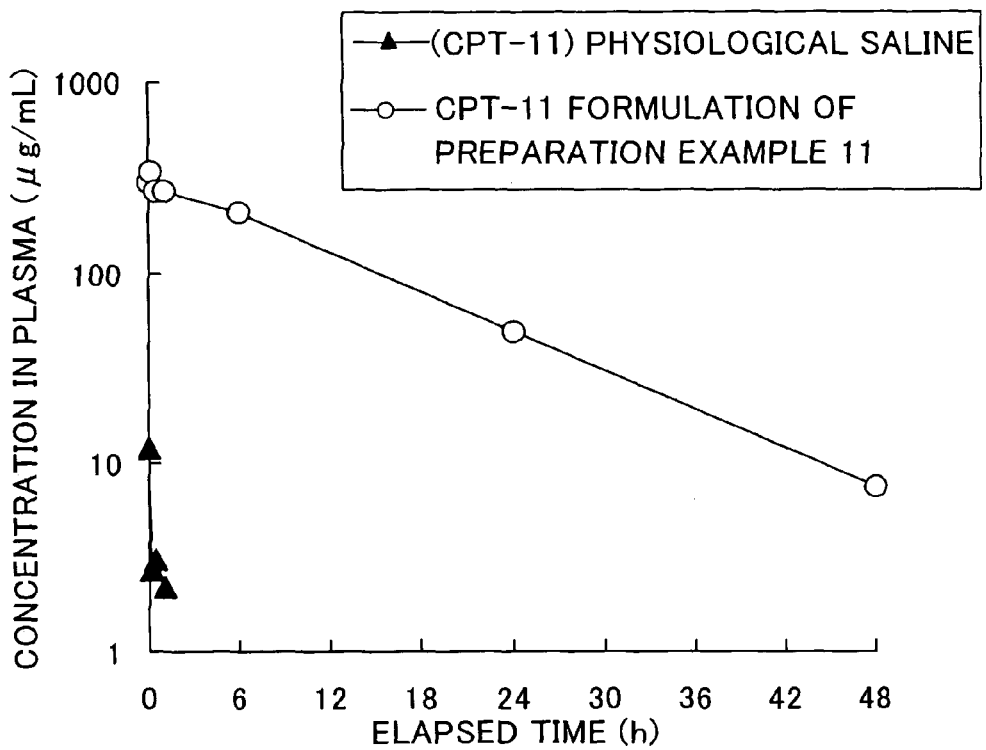
FIG. 8 This is a diagram showing transition of the total CPT-11 concentration in blood plasma in a pharmacokinetics experiment in Example 8.

In the physiological saline solution of irinotecan hydrochloride, the total CPT-11 concentration reduced rapidly after injection and reduced to less than the lower limit of quantification (<1 μg/mL) until 1 hour. Meanwhile, for the CPT-11 preparation, the total CPT-11 concentration reduced exponentially from 1 to 48 hours after injection, and sufficient extension of retention time was recognized as compared with that of the physiological saline solution of irinotecan hydrochloride (FIG. 8).

Figure 9:
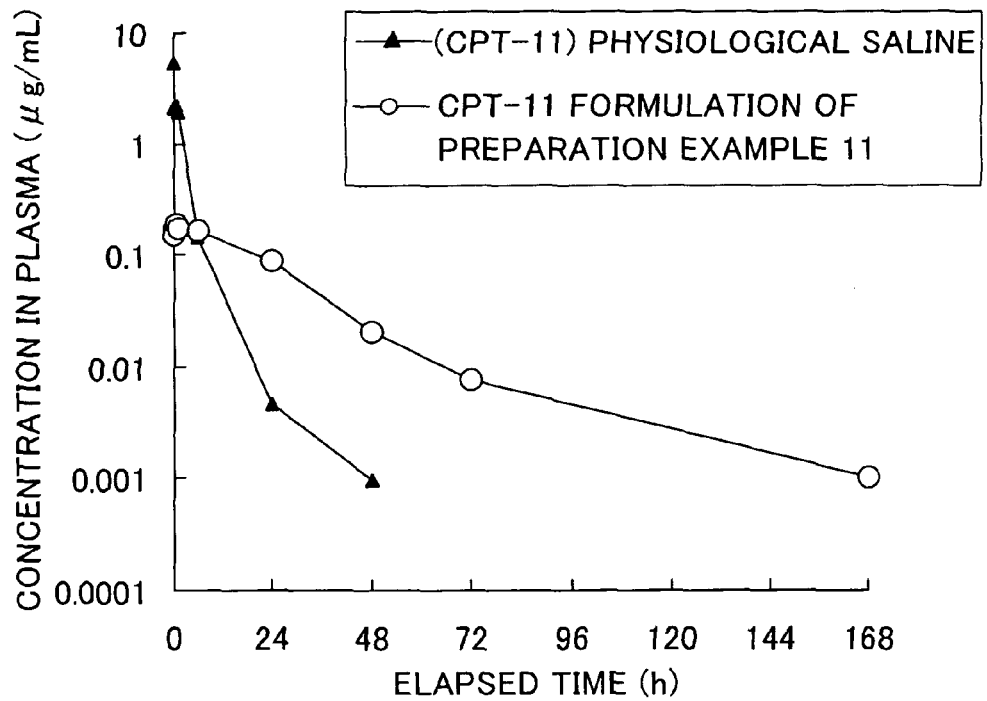
FIG. 9 This is a diagram showing transition of the liposome-released CPT-11 concentration in blood plasma in a pharmacokinetics experiment of the CPT-11 preparation in Example 8.

In the physiological saline solution of irinotecan hydrochloride, the free CPT-11 concentration reduced relatively quickly until 6 hours after achieving the highest concentration immediately after injection, after which the concentration reduced moderately. Meanwhile, in the CPT-11 preparation, the free CPT-11 concentration achieved the highest concentration in 1 hour after injection, and then reduced moderately (FIG. 9).

Figure 10:
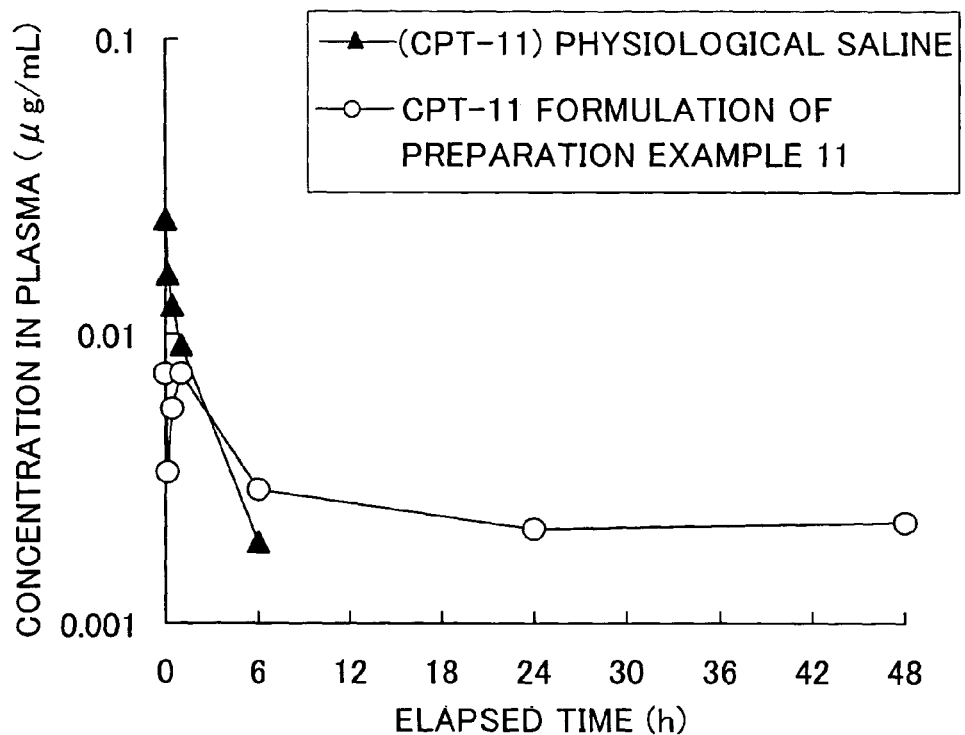
FIG. 10 This is a diagram showing transition of the SN-38 concentration in blood plasma in a pharmacokinetics experiment of the CPT-11 preparation in Example 8.

In the physiological saline solution of irinotecan hydrochloride, the SN-38 concentration reduced rapidly after achieving the highest concentration immediately after injection, and reduced to less than the lower limit of quantification (<0.0005 μg/mL) until 24 hours. Meanwhile, for the CPT-11 preparation, the SN-38 concentration was maintained for 1 hour after achieving the highest concentration immediately after injection. The concentration reduced after that, to be maintained from 6 to 48 hours (FIG. 10).

Figure 11:
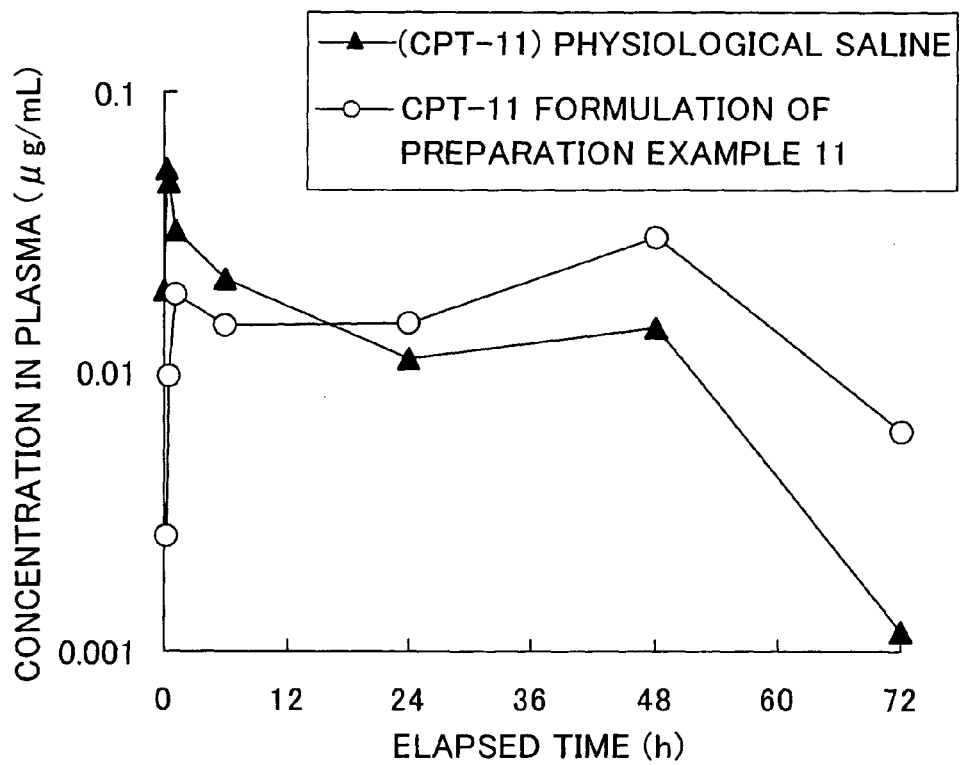
FIG. 11 This is a diagram showing transition of the SN-38G concentration in blood plasma in a pharmacokinetics experiment of the CPT-11 preparation in Example 8.

For both the CPT-11 preparation and the physiological saline solution of irinotecan hydrochloride, the SN-38G concentration increased in 1 hour after injection, to reduce slightly with maintain of the concentration (FIG. 11).

Test Example 8

Hemotoxicity

The CPT-11 preparation prepared in Preparation Example 11 was injected to a tail vein of the rat (CD(SD)IGS rat, male, 7 weeks old, Charles River Japan, Inc.) until satisfying a content of irinotecan hydrochloride with 3, 10, and 30 mg/kg, or satisfying the physiological saline solution of irinotecan hydrochloride with 30 mg/kg.

Figure 12:
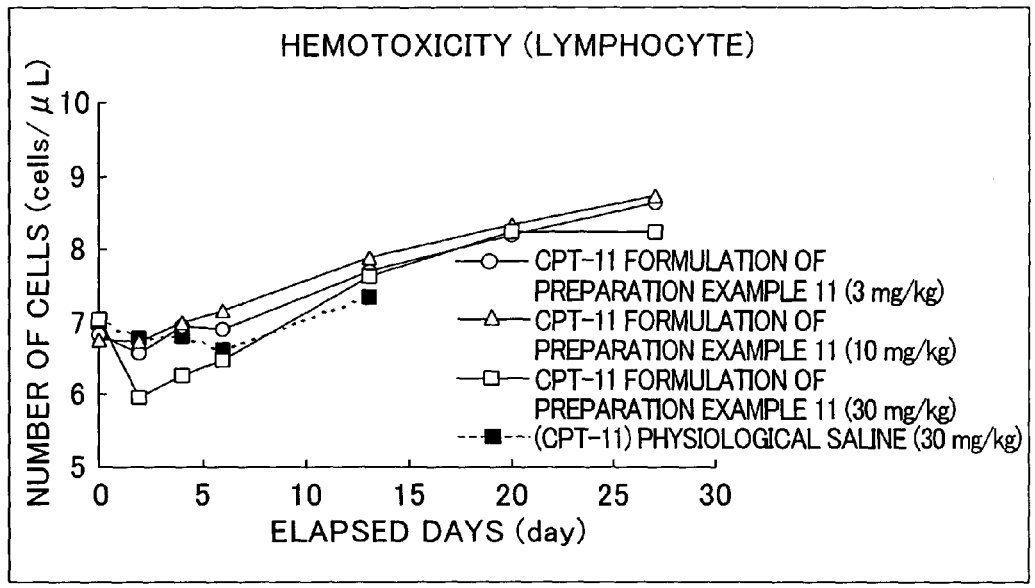
FIG. 12 This is a diagram showing hemotoxicity (lymphocyte) of the CPT-11 preparation prepared in Example 8.
Figure 13:
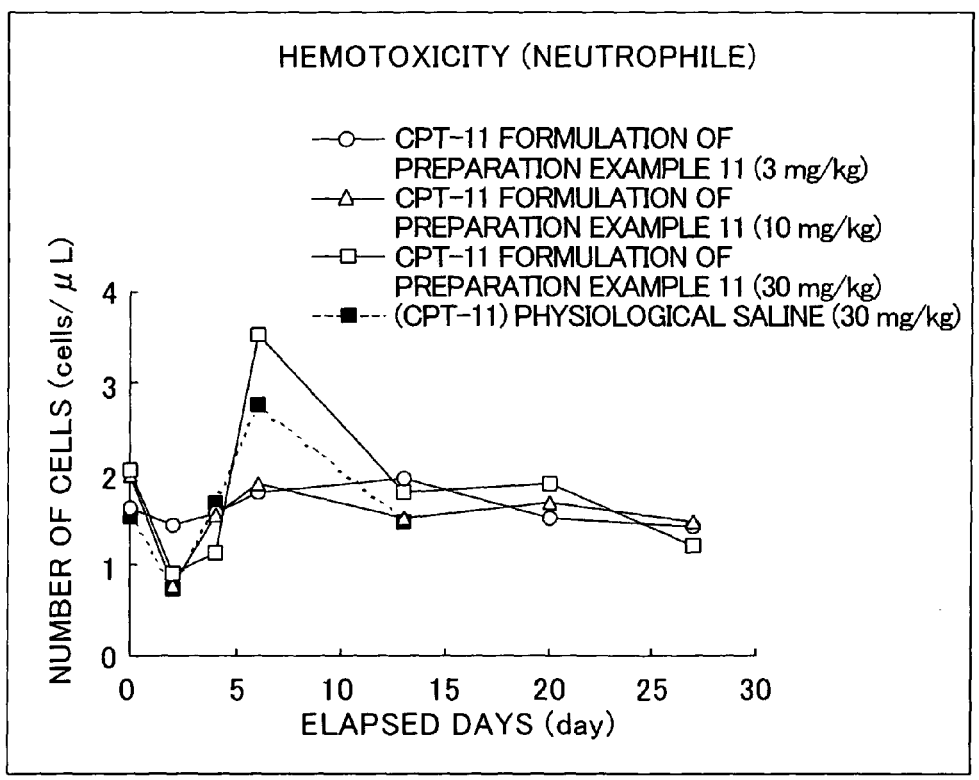
FIG. 13 This is a diagram showing hemotoxicity (neutrophil) of the CPT-11 preparation prepared in Example 8.

Collecting blood of 0.4 mL from a cervical vein of the rat before and after injection; and after 2, 4, 6, 13, 20, and 27 days (for 4 weeks); the number of neutrophils and lymphocytes was measured with automated hematology analyzer (Sysmex XT-2000i, Sysmex). FIGS. 12 and 13 show the results.

The number of neutrophils reduced transiently, to recover quickly after that with any injection amount. At a dose of 10 and 30 mg/kg as a content of irinotecan hydrochloride compared to 3 mg/kg of the content, extent of the number reduction was large. At a dose of 30 mg/kg, the number increased rapidly in the recovery period. In 30 mg/kg each of both injection agents, significant differences between transitions in the number of neutrophils were not recognized (FIG. 12). The number of lymphocytes was on a decline immediately after injection albeit only slightly. However, there was no difference between injections (FIG. 13).

The results above described recognized transient weak hematoxicity for neutrophils in the CPT-11 preparation. However, intensity of hematoxicity was approximately equal to that in the same amount of the physiological saline solution of irinotecan hydrochloride.

Example 9

Preparation Example 12

(1) Preparation of Liposome 65.250 g of HSPC, 26.800 g of Chol and 8.000 g of TRX-20 were weighed, and 100 mL of absolute ethanol was added thereto. Then, those were dissolved with heating at 68° C. After confirming that those were dissolved completely, 900 mL of ammonium sulfate solution (250 mM) was added thereto, and the mixture was stirred with heating at 68° C.

(2) Regulation of Particle Size of Liposome

Regulation of particle size of liposome: after completion of the stirring with heating, the resultant mixture was passed through a filter having a pore size of 100 nm five times using an extruder heated to 68° C.

Introduction of $PEG_{5000}$-DSPE: after the extrusion, to the sample was added 200 mL of a $PEG_{5000}$-DSPE solution (36.74 mg/mL) so as to be a predetermined $PEG_{5000}$-DSPE content (mol %), and the mixture was stirred at 60° C. for 30 minutes, to thereby introduce $PEG_{5000}$-DSPE. After the introduction, the sample was cooled in ice.

(3) Outer Aqueous Phase Substitution

For the ice-cooled sample, outer aqueous phase substitution was performed using a cross flow filtration system with an outer aqueous phase solution (10 mM histidine/10% sucrose solution) (pH 6.5). After the outer aqueous phase substitution, the HSPC concentration and the Cholesterol concentration was determined using a high performance liquid chromatography. An amount of irinotecan hydrochloride that should be encapsulated was calculated from the summation of the HSPC concentration, the Cholesterol concentration and the TRX-20 concentration as the total lipid concentration.

(4) Drug Encapsulation

There was prepared an irinotecan hydrochloride (CPT-11)/ RO water (reverse osmosis membrane purified water) solution having a concentration of 10 mg/mL. The irinotecan hydrochloride solution was added to the liposome dispersion in an amount of CPT-11/total lipids amount=0.16 (mol/mol) with respect to the total lipids amount (mM) above, and the mixture was stirred at 50° C. for 20 minutes, to thereby introduce irinotecan hydrochloride. After the introduction, the sample was cooled in ice.

(5) Removal of Unencapsulated Drug

After the encapsulation of irinotecan hydrochloride, to the liposome dispersion was added the outer aqueous phase solution, and removal of unencapsulated drug was performed using a cross flow filtration system.

(6) Regulation of Concentration

For the liposome dispersion after the removal of unencapsulated drugs, an amount of irinotecan hydrochloride was determined using a high performance liquid chromatography and regulated to 5.0 mg/mL of irinotecan hydrochloride concentration.

(7) Filter Sterilization

After the regulation of concentration, the liposome dispersion was filled into a vial tube through a filter sterilization using a sterilizing filter having a pore size of 0.2 μm.

The composition and particle size of the CPT-11 formulation obtained above are shown in Table 11.

TABLE 11

| | Initial membrane composition (molar ratio) | | Lipid concentration | | Supported drug | | |
|---|---|---|---|---|---|---|---|
| | Lipid HSPC:Chol:TRX-20 | PEG-DSPE | (HSPC) Phospholipid mg/mL | Total lipid mM | Drug concentration mg/mL | amount Drug mol/total lipid mol | Particle size nm |
| Preparation Example 12 | 50:42:8 | 0.75 | 18 | 44 | 4.66 | 0.15 | 92.0 |

Test Example 9

Antitumor Effect $2\times10^6$ cells/mouse of human colon cancer cells (HCT116) were implanted subcutaneously in left inguinal region of the mouse (BALB/c nude, ♂, 6 weeks old, Charles River Japan, Inc.). After implanting tumors, a presumptive tumor volume was calculated by $\frac{1}{2}\cdot ab^2$ (a represents a longitudinal diameter of a tumor and b represents a short axis diameter thereof) achieved to about 90 mm³ in a day (Day 0). From the next day, at 3 times in all every four days (Days 1, 5, and 9), a CPT-11 preparation prepared in Preparation Example 12 or a physiological saline solution of irinotecan hydrochloride was injected to a tail vein of the mouse. There were mice without injection of either agent as a control group.

A presumptive tumor volume and a body weight of a mouse were measured after 5, 8, 12, 16, and 21 days from the injection. Extracting tumors 21 days after the injection and measuring a weight thereof, further, an inhibition rate of tumor growth I.R. (%) was calculated by the formula as shown in Test Example 6.

Figure 14:
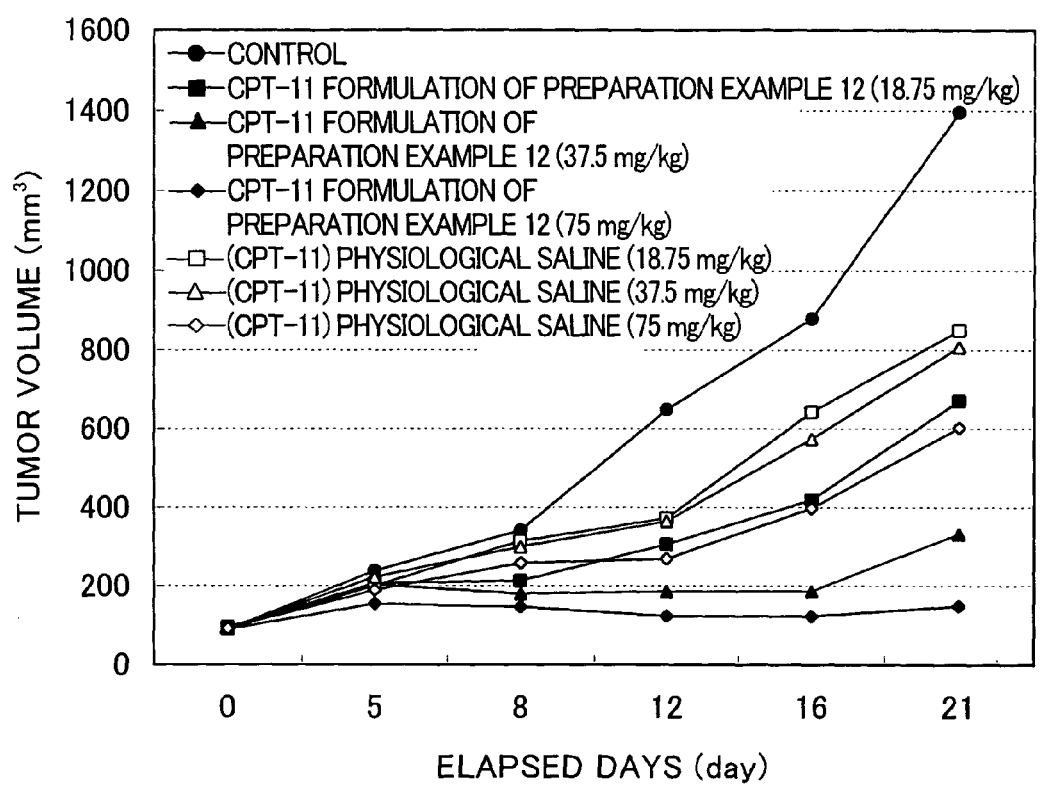
FIG. 14 This is a diagram showing antitumor effect of the CPT-11 preparation prepared in Example 9 by change of presumptive tumor volume with time.
Figure 15:
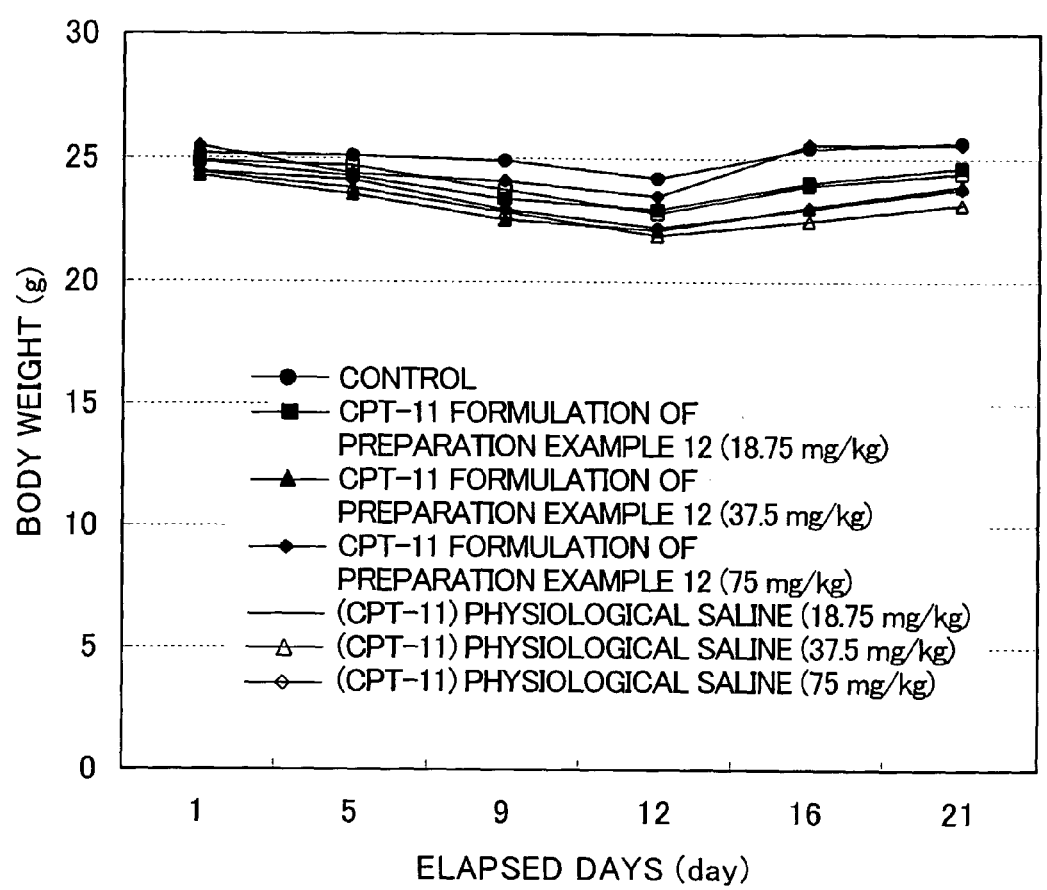
FIG. 15 This is a diagram showing antitumor effect of the CPT-11 preparation prepared in Example 9 by change of a body weight of the mouse.

Table 12 and FIGS. 14 and 15 show the results.

The CPT-11 preparation and the physiological saline solution of irinotecan hydrochloride each proved a significant suppressive effect of tumor growth for human colon cancer with the treatment group compared to the control group. The CPT-11 preparation proved higher antitumor effect than that of the physiological saline solution of irinotecan hydrochloride (Table 12, FIG. 14). Further, either agent did not influence the body weight of the mouse (FIG. 15).

TABLE 12

|  | Dose (mg/kg) | Tumor weight (g, mean ± S.D.) | Inhibition rate (%) |
|---|---|---|---|
| Control group | — | 1.25 ± 0.15 | — |
| CPT-11 preparation (Preparation Example 12) | 18.75 | 0.61 ± 0.11 | 51.1 |
|  | 37.5 | 0.36 ± 0.07 | 70.8 |
|  | 75 | 0.14 ± 0.03 | 88.7 |
| Physiological saline solution of irinotecan hydrochloride | 18.75 | 0.76 ± 0.06 | 39.0 |
|  | 37.5 | 0.71 ± 0.08 | 43.4 |
|  | 75 | 0.53 ± 0.14 | 57.4 |

Test Example 10

Pharmacokinetics Due to Single Administration

After applying cannulas to femoral vein and femoral vein of the rat (CD(SD)IGS rat, male, 7 weeks old, Charles River Japan, Inc.) under anesthesia, and setting the rat in bollman-cage, the CPT-11 preparation prepared in Preparation Example 12 or the physiological saline solution of irinotecan hydrochloride was intravenously injected though a femoral vein cannula to the rat until satisfying a content of irinotecan hydrochloride with 3, 10, and 30 mg/kg.

Collecting blood from the rat after injection; after 2, 10, and 30 min; and after 1, 3, 6, 9, 24, and 30 hours; 50 μL of blood plasma was obtained by centrifugal separation, to be diluted with 200 μL of an internal standard solution. After providing 50 μL of the blood plasma diluted with the internal standard solution with 500 μL of methanol and stirring, the diluted blood plasma was diluted with 0.146 M $H_3PO_4$ 10-fold as a sample for total CPT-11 concentration measurement. Meanwhile, subjecting 200 μL of the diluted blood plasma to centrifugal separation (100,000×g, for 30 min, 10° C.), and the obtained 50 μL in upper layer was diluted with 0.146 M $H_3PO_4$ 10-fold as samples for free CPT-11 concentration measurement, SN-38 concentration measurement, and SN-38G concentration measurement. The samples obtained were measured each concentration thereof with PROSPEKT-HPLC in accordance with methods such as Kurita method (J. Chromatogr. B 724, p 335 to 344, 1999). FIGS. 16 to 19 show the results.

Figure 16:
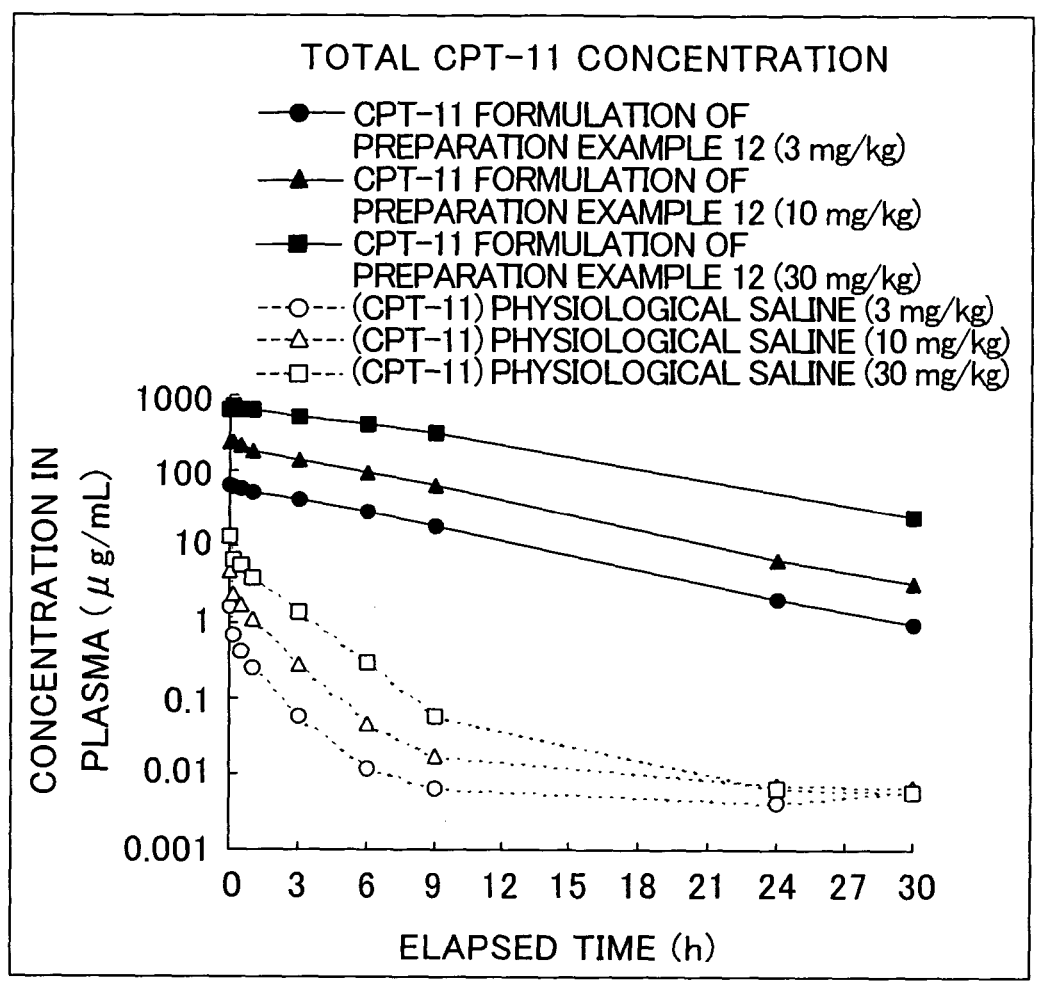
FIG. 16 This is a diagram showing transition of the total CPT-11 concentration in blood plasma in a pharmacokinetics experiment of the CPT-11 preparation in Example 9.

In the physiological saline solution of irinotecan hydrochloride, the total CPT-11 concentration reduced rapidly after injection and reduced exponentially from 0.5 to 9 hours with any injection amount (3, 10 and 30 mg/kg). Meanwhile, for the CPT-11 preparation, the total CPT-11 concentration reduced almost exponentially from 10 min to 30 hours after injection, and sufficient extension of retention time was recognized as compared with that of the physiological saline solution of irinotecan hydrochloride (FIG. 16).

Figure 17:
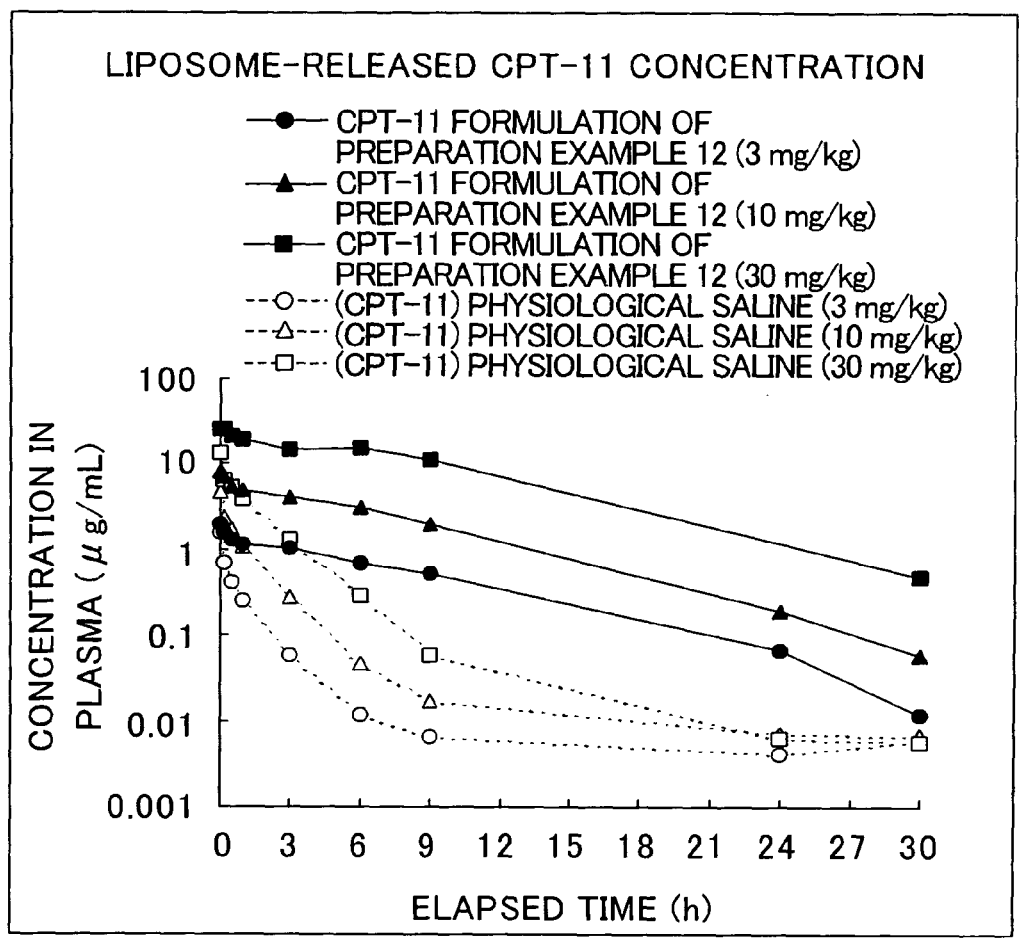
FIG. 17 This is a diagram showing transition of the liposome-released CPT-11 concentration in blood plasma in a pharmacokinetics experiment of the CPT-11 preparation in Example 9.

The liposome-released CPT-11 concentration reduced almost exponentially from 10 min to 30 hours after injection of the CPT-11 preparation, and sufficient extension of retention time was recognized as compared with that of the physiological saline solution of irinotecan hydrochloride (FIG. 17).

Figure 18:
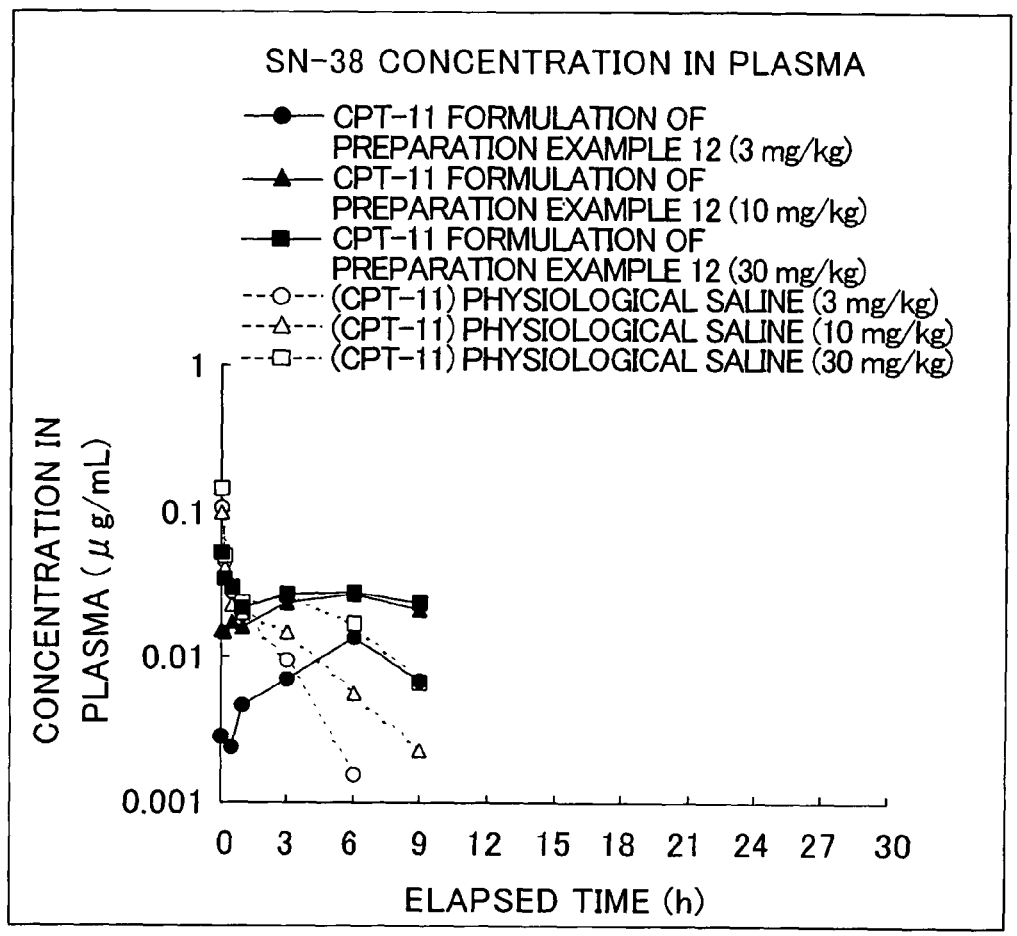
FIG. 18 This is a diagram showing transition of the SN-38 concentration in blood plasma in a pharmacokinetics experiment of the CPT-11 preparation in Example 9.

In the physiological saline solution of irinotecan hydrochloride, the SN-38 concentration reduced rapidly, just after injection, and reduced moderately after 1 hour with any injection amount, to be approximately conserved to 3 hours with 30 mg/kg. Meanwhile, for the CPT-11 preparation, the SN-38 concentration reduced moderately after achieving the highest concentration from 3 to 6 hours after injection at doses of 3 and 10 mg/kg, respectively. The concentration reduced rapidly for 1 hour after achieving the highest concentration immediately after injection, to be approximately conserved to 9 hours at a dose of 30 mg/kg (FIG. 18).

Figure 19:
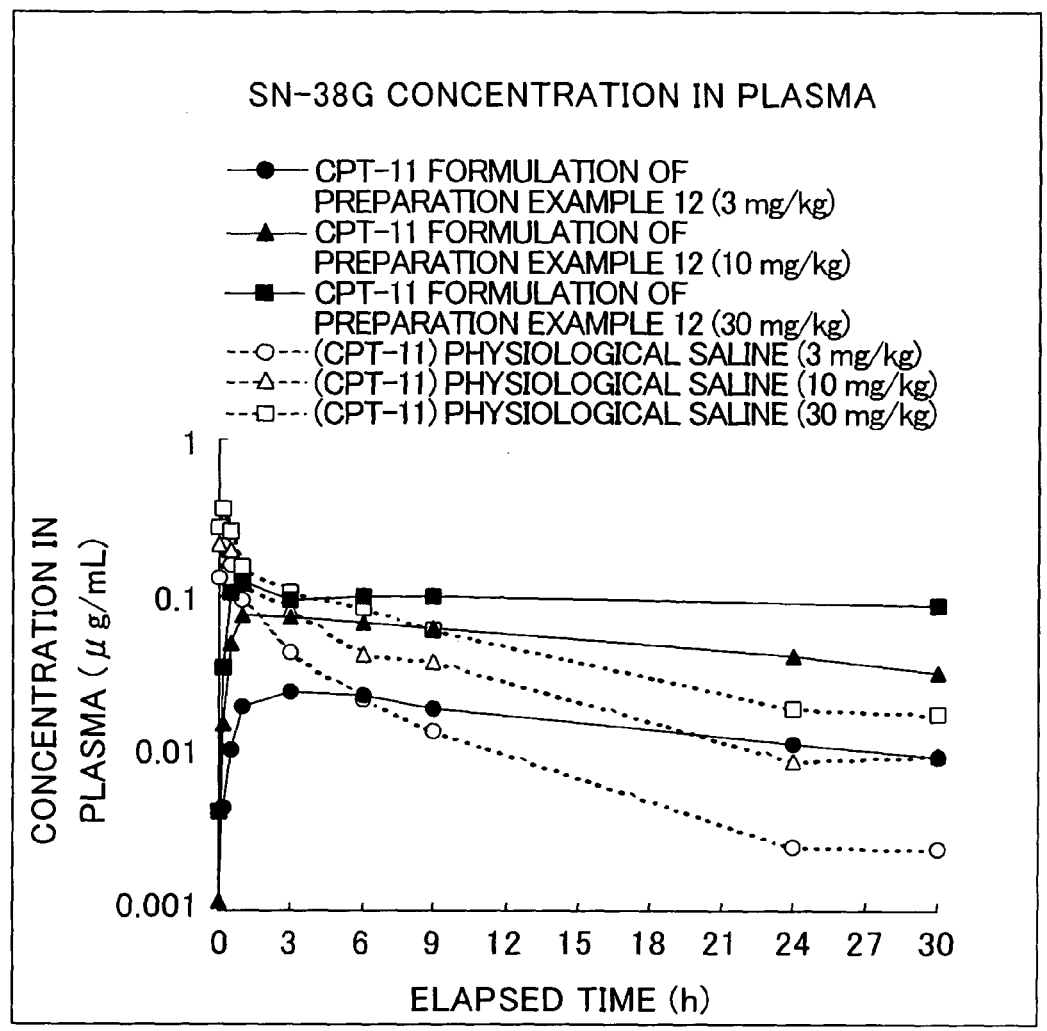
FIG. 19 This is a diagram showing transition of the SN-38G concentration in blood plasma in a pharmacokinetics experiment of the CPT-11 preparation in Example 9.

In the physiological saline solution of irinotecan hydrochloride, the SN-38G concentration reduced quickly to 1 hours after achieving the highest concentration at 10 min after injection with any injection amount, to reduce moderately after that. Meanwhile, for the CPT-11 preparation, the SN-38G concentration increased to 1 hours after injection, to reduce slightly with maintain of concentration (FIG. 19).

Example 10

The CPT-11 formulation prepared in Preparation Example 9 as the CPT-11 highly supported formulation of the present invention was tested.

Test Example 11

Antitumor Effect

Human colon cancer cells (HT-29) with 2 to 3 mm square were transplanted subcutaneously in an inguinal region of a mouse (BALB/c nude, male, 6 weeks old, CLEA Japan, Inc.) with a needle for transplantation. The CPT-11 formulation prepared in Preparation Example 9 or a physiological saline solution of irinotecan hydrochloride was injected into a caudal vein three times in total which were a point (day 1) at which an estimated volume of tumors calculated by $\frac{1}{2}\cdot ab^2$ (a refers to as a major axis of each tumor, b refers to as a miner axis) approached to of around 100 mm³, an additional 4 days (day 5), and additional 8 days (day 9), after the transplantation of tumors. Mice without injection of either agent were employed as a control group.

The estimated volume of tumors and a body weight of the mouse were calculated at 4, 8, 12, 17, 21 days after a first injection. The tumors were also removed 21 days after the injection and the weight of the tumors were measured, to thereby calculate a tumor proliferation inhibition rate, I.R. (%) by the formula as shown in Test Example 6.

Figure 20:
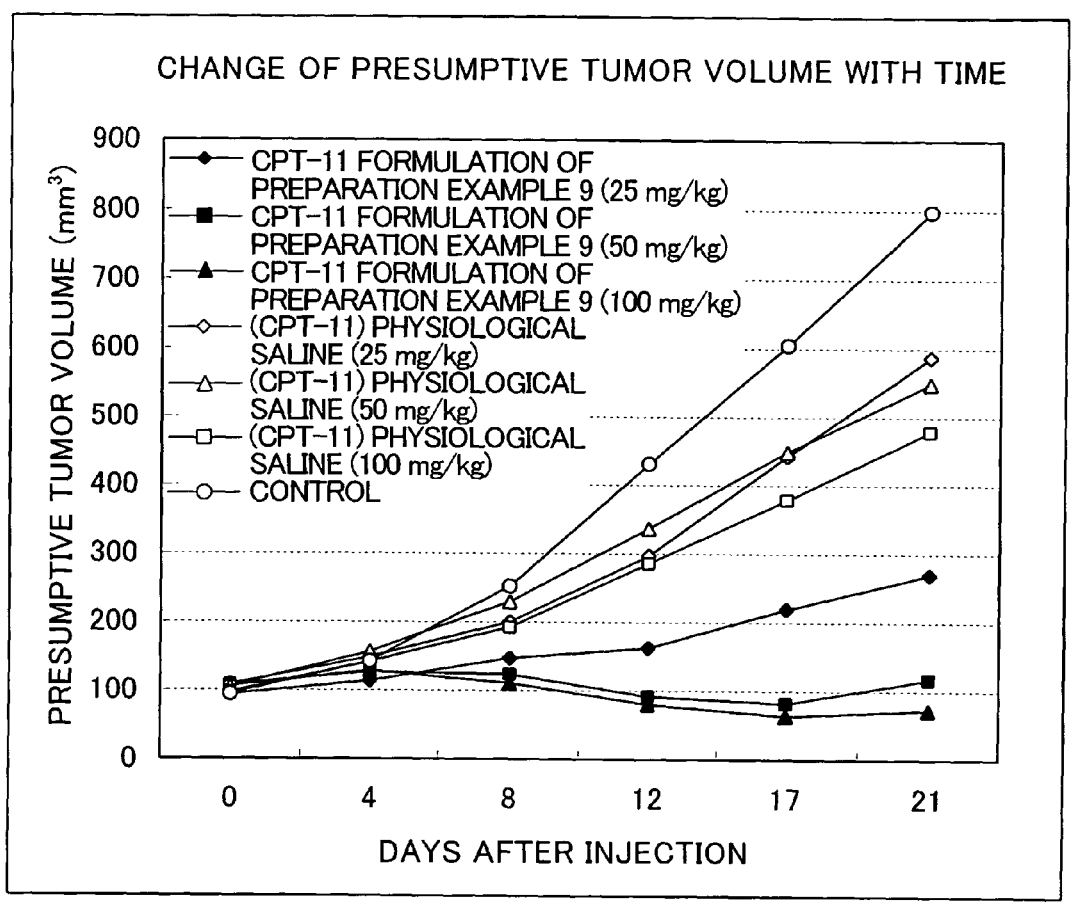
FIG. 20 This is a diagram showing antitumor effect of the CPT-11 preparation by change of presumptive tumor volume with time in Example 10.
Figure 21:
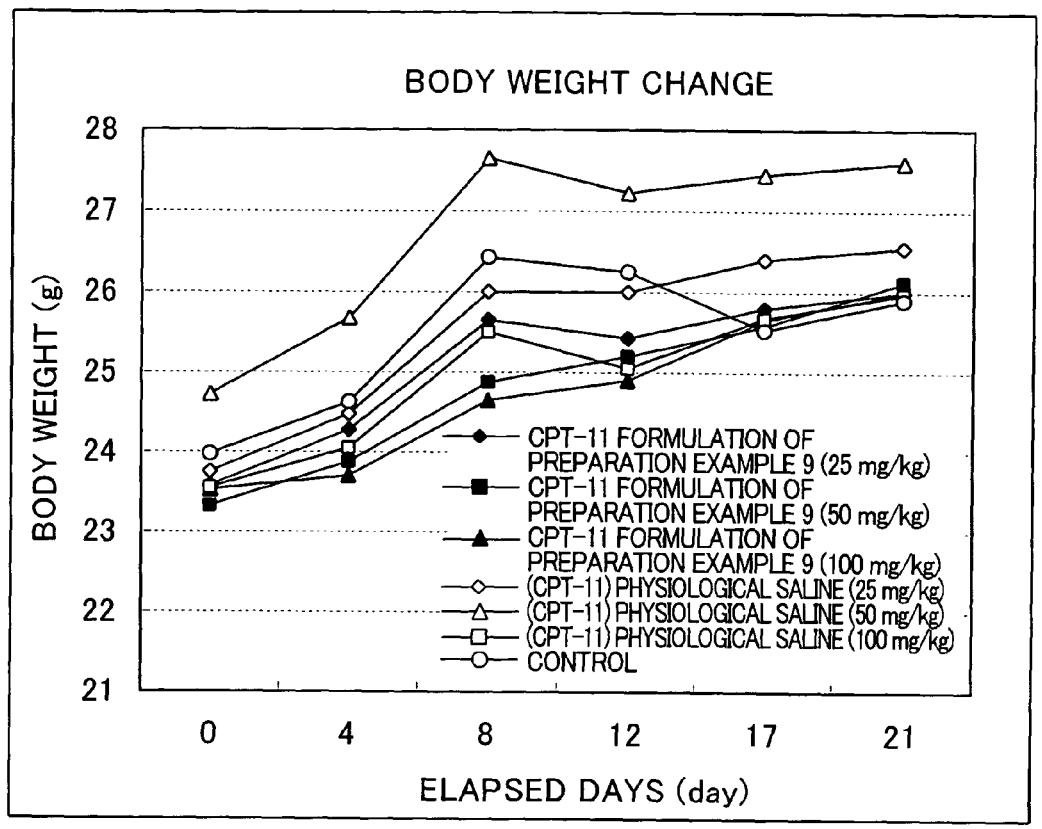
FIG. 21 This is a diagram showing antitumor effect of the CPT-11 preparation by change of a body weight of the mouse in Example 10.

The results are shown in Table 13, FIG. 20, and FIG. 21.

In the human colon cancer, the CPT-11 formulation and the physiological saline solution of irinotecan hydrochloride each showed a strong tumor proliferation inhibitory effect compared with the control group. Further, the CPT-11 formulation revealed a high antitumor effect compared with that of the physiological saline solution of irinotecan hydrochloride (Table 13, FIG. 20). Further, either agent didn't affect the body weight of the mouse (FIG. 21).

TABLE 13

|  | Dose (mg/kg) | Tumor weight (g, mean ± S.D.) | Inhibition rate (%) |
|---|---|---|---|
| Control group | — | 0.58 ± 0.29 | — |
| CPT-11 formulation | 25 | 0.18 ± 0.15 | 69.4 |
| (Preparation Example 9) | 50 | 0.09 ± 0.06 | 84.1 |
|  | 100 | 0.05 ± 0.03 | 92.0 |
| Physiological saline | 25 | 0.36 ± 0.41 | 38.2 |
| solution of irinotecan | 50 | 0.44 ± 0.36 | 24.9 |
| hydrochloride | 100 | 0.33 ± 0.32 | 44.0 |

Test Example 12

Pharmacokinetics Due to Single Administration

Mouse fibrosarcoma (Meth A), $2.5 \times 10^5$ cells/mouse were transplanted subcutaneously in an inguinal region of a mouse (BALB/c, female, 7 weeks old, Japan SLC, Inc.). The tumors were left to grow in 20 days after the tumors transplantation, and then the CPT-11 formulation prepared in Preparation Example 9 or a physiological saline solution of irinotecan hydrochloride was administered into a caudal vein with 10 mg/kg as a concentration of irinotecan hydrochloride.

After administration, blood in a heart was collected after 10, and 30 minutes, and 1, 3, 6, 12, 24, 48, and 96 hours, and was treated in a centrifuge (15,000 rpm, 1 minute, 0° C.), to thereby obtain plasma. The obtained plasma was diluted 50-fold with 0.146 M $H_3PO_4$, and was added to an equal amount of internal standard solution, as a sample for measurement of CPT-11 concentration in the plasma of an animal administered with the CPT-11 formulation. The obtained plasma was diluted 4-fold with 0.146 M $H_3PO_4$, and was added to an equal amount of internal standard solution, as a sample for measurement of an SN-38 concentration and an SN-38G concentration each in the plasma of the animal administered with the CPT-11 formulation, and a drug concentration in the plasma of the animal administered with the physiological saline solution of irinotecan hydrochloride.

After blood in the heart was collected, tumors were removed from the inguinal area and washed with physiological saline, and then tumor weight was measured. The resultant tumor was added to an amount of 5 times of cooled 0.146 M.$H_3PO_4$, and homogenized with a teflon homogenizer. 200 μL of the resulting homogenized tumor was added to 50 μL of internal standard solution and 0.75 ml of methanol, suspended, and then left to stand for over night at −20° C. The resultant solution was treated in a centrifuge (15,000 rpm, 3 minutes, 0° C.) prior to added 0.4 mL of 0.146 M $H_3PO_4$ to 0.1 mL of supernatant, to thereby obtain a sample for HPLC measurement. Each concentration of the resultant sample for measurement was measured with a PROSPEKT-HPLC according to Kurita method (J Chromoatogr B 724, pp. 335-344, 1999.), or the like. The results are shown in FIGS. 22 to 27.

Figure 22:
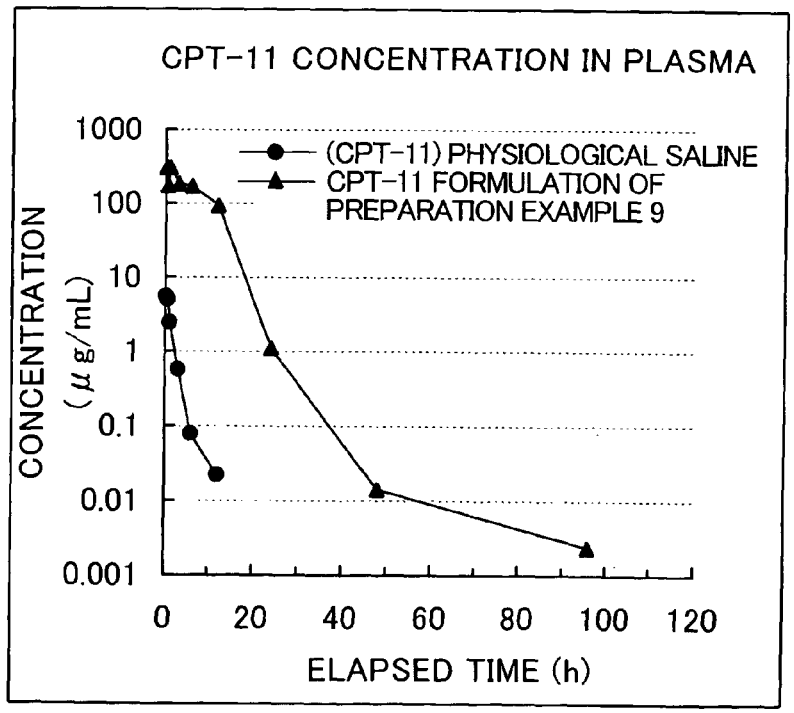
FIG. 22 This is a diagram showing transition of the CPT-11 concentration in blood plasma in a pharmacokinetics experiment of the CPT-11 preparation in Example 10.
Figure 23:
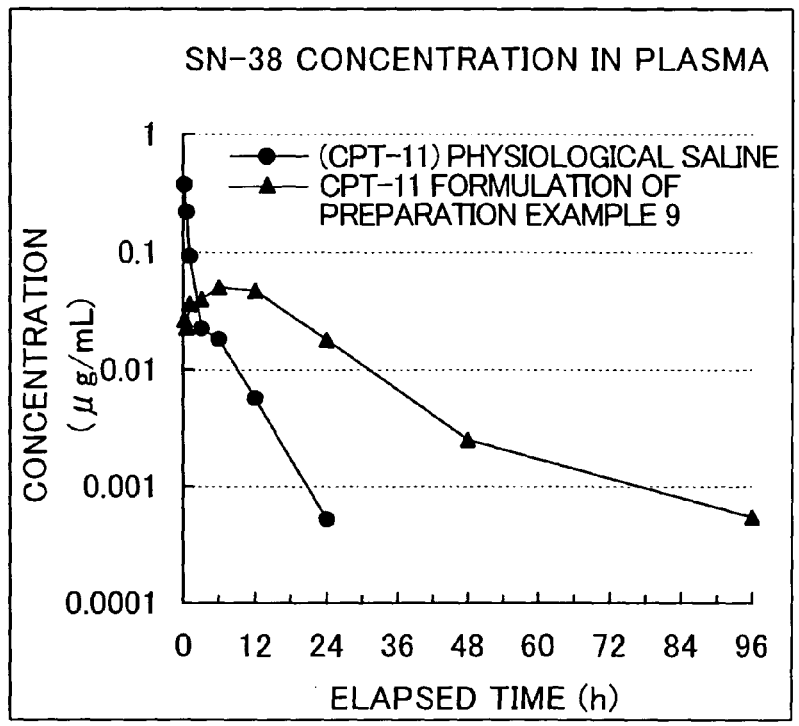
FIG. 23 This is a diagram showing transition of the SN-38 concentration in blood plasma in a pharmacokinetics experiment of the CPT-11 preparation in Example 10.
Figure 24:
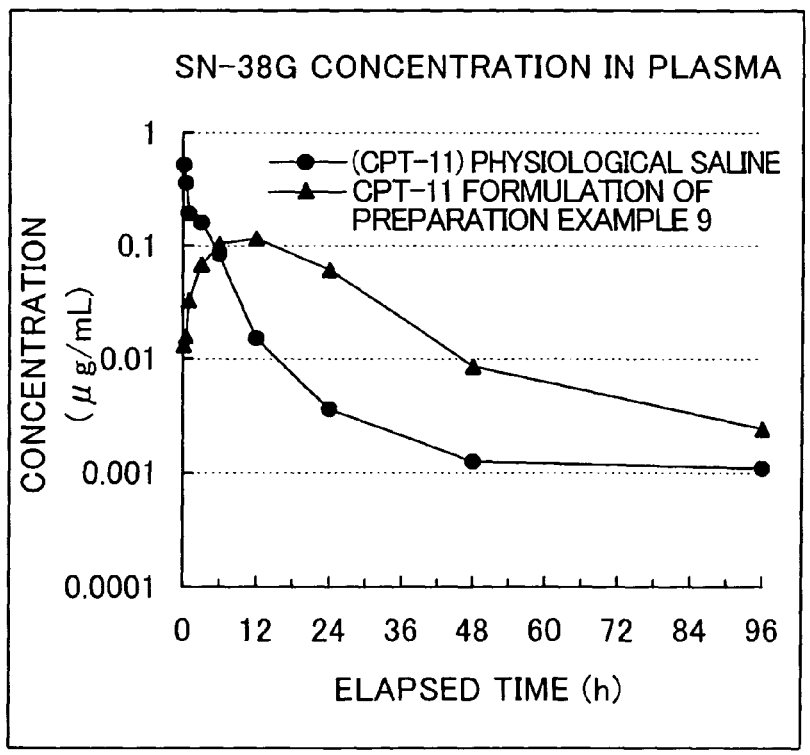
FIG. 24 This is a diagram showing transition of the SN-38G concentration in blood plasma in a pharmacokinetics experiment of the CPT-11 preparation in Example 10.

The CPT-11 formulation increased an area under the concentration in the plasma-time curve up to 302-fold, and a mean resident time up to 4.4-fold compared with those of the physiological saline solution of irinotecan hydrochloride, respectively, owing to liposome formulation, in the concentration of CPT-11 in the plasma (FIG. 22). Meanwhile, preparation as a liposome formulation increased an area under the concentration in the plasma-time curve up to 2.5-fold as for the concentration of SN-38 in the plasma, and extended a mean resident time (FIG. 23). Further, preparation as a liposome formulation increased an area under the concentration in the plasma-time curve up to 1.8-fold as for the concentration of SN-38G in the plasma, and extended a mean resident time (FIG. 24).

Figure 25:
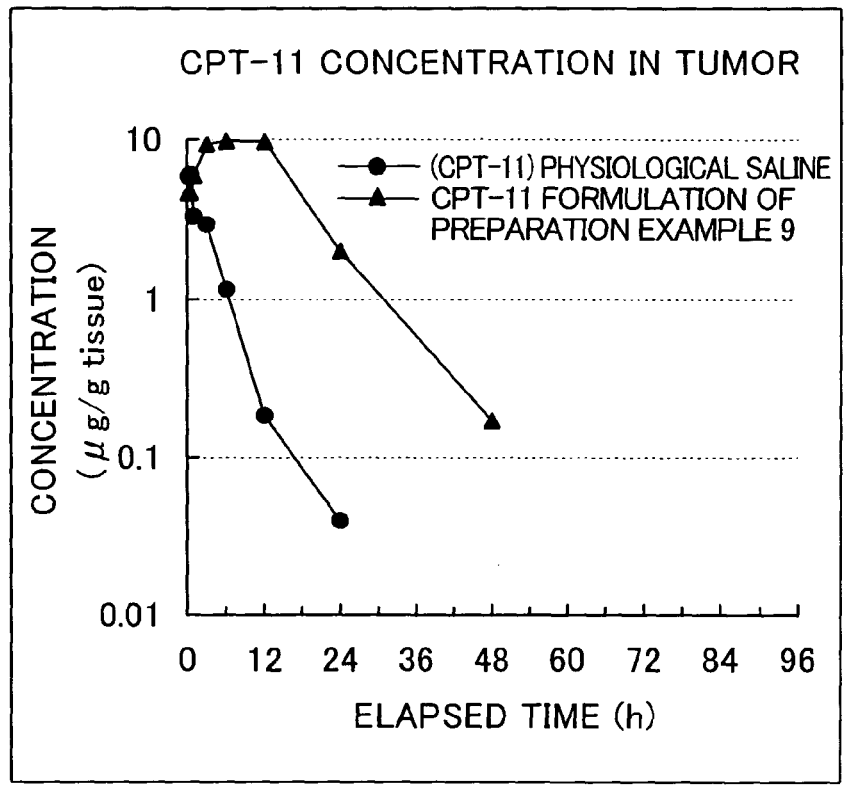
FIG. 25 This is a diagram showing transition of the CPT-11 concentration in tumors in a pharmacokinetics experiment of the CPT-11 preparation in Example 10.

In the physiological saline solution of irinotecan hydrochloride, a concentration of irinotecan hydrochloride in the tumor tissues became a maximum concentration level in the tumor tissue at 0.5 hours after administration, and then decreased with 2.3 hours of half-life. Meanwhile, in the CPT-11 formulation, the concentration increased gradually, and reached a maximum concentration level in the tumor tissue after 12 hours, and then decreased more mildly than that of the physiological saline solution of irinotecan hydrochloride, to increase an area under the concentration in the tumor tissue-time curve 9.0-fold (FIG. 25).

Figure 26:
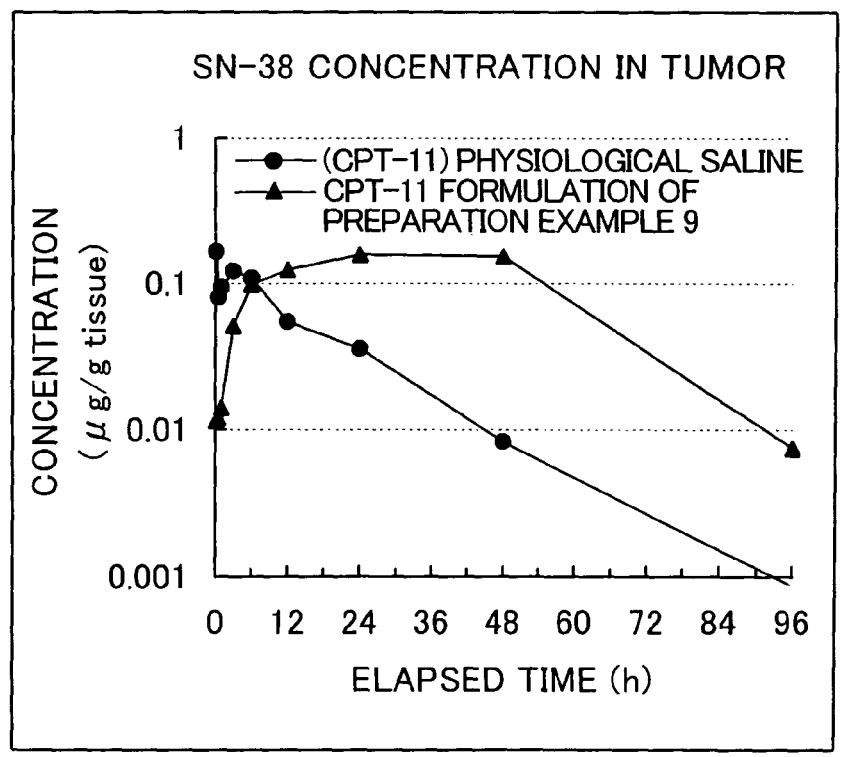
FIG. 26 This is a diagram showing transition of the SN-38 concentration in tumors in a pharmacokinetics experiment of the CPT-11 preparation in Example 10.

In the physiological saline solution of irinotecan hydrochloride, a concentration of SN-38 in the tumor tissues reached a maximum concentration in the tumor tissue at 10 minutes after administration, and then decreased gradually. In the CPT-11 formulation, the concentration increased gradually to 6 hours after administration, and then maintained a constant concentration approximately to 48 hours. Thereafter, the concentration decreased at extinction of a half-life in nearly the same way as that of the physiological saline solution of irinotecan hydrochloride, to increase an area under the concentration in the tumor tissue-time curve 3.9-fold (FIG. 26).

Figure 27:
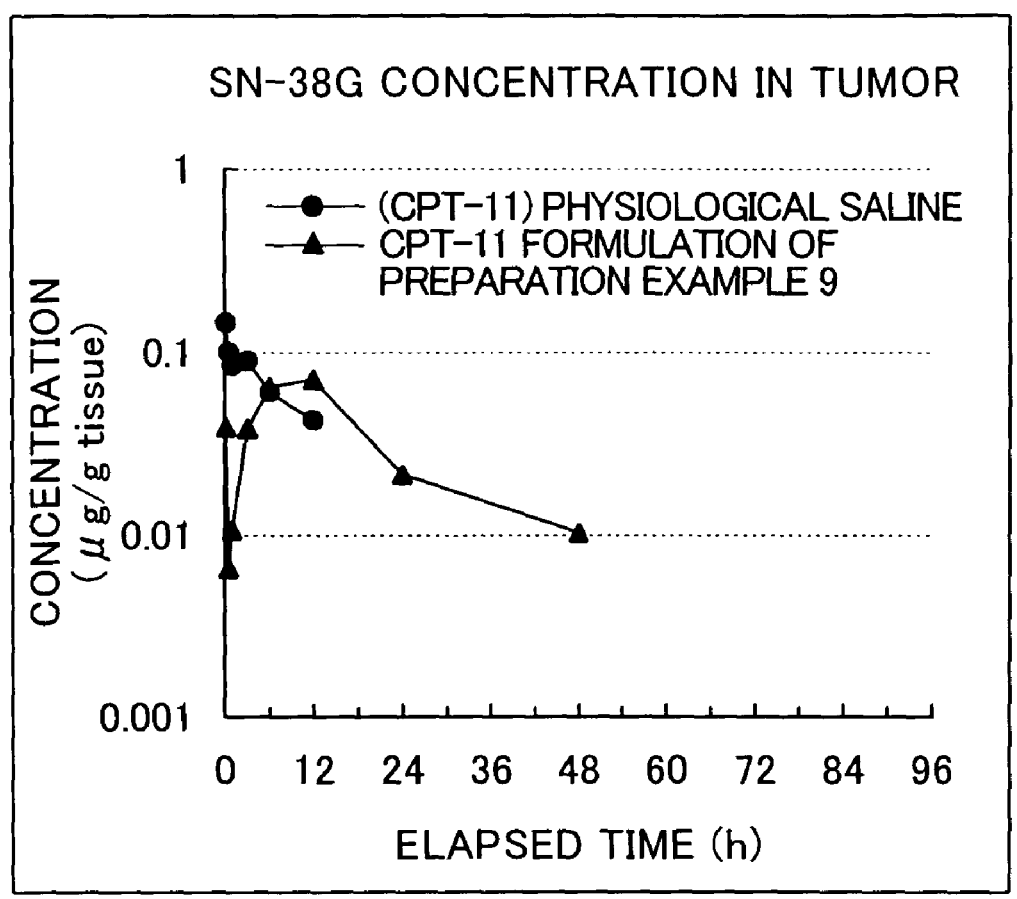
FIG. 27 This is a diagram showing transition of the SN-38G concentration in tumors in a pharmacokinetics experiment of the CPT-11 preparation in Example 10.

In the physiological saline solution of irinotecan hydrochloride, a concentration of the SN-38G in the tumor tissues reached a maximum concentration in the tumor tissues at 10 minutes after administration, and then decreased gradually. In the CPT-11 formulation, the concentration increased gradually, reached a maximum concentration in the tumor tissue at 12 hours after administration, and then decreased gradually (FIG. 27).

Therefore, it was confirmed that the retentivity in blood and tumor transitional properties in the CPT-11 formulation were higher than those of the physiological saline solution of irinotecan hydrochloride.

Example 11

The CPT-11 formulation prepared in Preparation Example 7 as the CPT-11 highly supported formulation of the present invention was tested.

Test Example 13

Antitumor Effect Due to Administration of a Drug Three Times

Mouse fibrosarcoma (Meth A), $2.5 \times 10^5$ cells/mouse were transplanted subcutaneously in an inguinal region of a mouse (BALB/c, female, 7 weeks old, CLEA Japan, Inc.). The CPT- 11 formulation prepared in Preparation Example 7 or a physiological saline solution of irinotecan hydrochloride was injected into a caudal vein three times in total, that is, 7, 9, and 11 days or 7, 11, and 15 days after transplantation of tumors. Mice without injection of either agent were employed as a control group.

The tumors were also removed after 21 days from the transplantation and weight of the tumors was measured, to thereby calculate each tumor proliferation inhibition rate, I.R. (%) by the formula as shown in Test Example 6. The results are shown in Table 14.

In the mouse fibrosarcoma, the CPT-11 formulation and the physiological saline solution of irinotecan hydrochloride each showed a significant tumor proliferation inhibitory effect compared to the control group. Further, the CPT-11 formulation exhibited a higher antitumor effect than that of the physiological saline solution of irinotecan hydrochloride. Further, either agent didn't affect the body weight of the mouse.

TABLE 14

| | Dose (mg/kg) | Treatment on days | Tumor weight (g, mean ± S.D.) | Inhibition rate (%) |
|---|---|---|---|---|
| Control group | — | — | 2.01 ± 0.30 | — |
| CPT-11 formulation (Preparation Example 7) | 50 | 7, 9, 11 | 0.20 ± 0.17 | 89.9 |
|  | 100 | 7, 9, 11 | 0.08 ± 0.01 | 96.2 |
| Physiological saline solution of irinotecan hydrochloride | 50 | 7, 9, 11 | 1.47 ± 0.18 | 26.9 |
|  | 100 | 7, 9, 11 | 0.28 ± 0.42 | 86.0 |
| CPT-11 formulation (Preparation Example 7) | 50 | 7, 11, 15 | 0.81 ± 0.47 | 59.6 |
|  | 100 | 7, 11, 15 | 0.16 ± 0.12 | 92.3 |
| Physiological saline solution of irinotecan hydrochloride | 50 | 7, 11, 15 | 1.99 ± 0.47 | 1.0 |
|  | 100 | 7, 11, 15 | 1.26 ± 0.49 | 37.4 |

Test Example 14

Antitumor Effect Due to Administration of a Drug Once or Twice

Mouse fibrosarcoma (Meth A), $2.5 \times 10^5$ cells/mouse were transplanted subcutaneously in an inguinal region of a mouse (BALB/c, female, 7 weeks old, CLEA Japan, Inc.). The CPT-11 formulation prepared in Preparation Example 7 or a physiological saline solution of irinotecan hydrochloride was injected into a caudal vein at 7 and/or 11 days once or twice in total after transplantation of tumors. Mice without injection of any agent were employed as a control group.

The tumors were also removed after 21 days from the transplantation and weight of the tumors was measured, to thereby calculate tumor proliferation inhibition rate, I.R. (%) by the formula as shown in Test Example 6. The results are shown in Table 15.

In the mouse fibrosarcoma, the CPT-11 formulations and the physiological saline solutions of irinotecan hydrochloride each showed a significant tumor proliferation inhibitory effect compared to the control group unless a part of the physiological saline solutions of irinotecan hydrochloride.

Further, some of the CPT-11 formulations exhibited a higher antitumor effect than that of the physiological saline solutions of irinotecan hydrochloride. Further, either of the two kinds of agents didn't affect the body weight of the mouse.

TABLE 15

| | Dose (mg/kg) | Treatment on days | Tumor weight (g, mean ± S.D.) | Inhibition rate (%) |
|---|---|---|---|---|
| Control group | — | — | 3.53 ± 0.25 | — |
| CPT-11 formulation (Preparation Example 7) | 12.5 | 7 | 1.95 ± 0.29 | 44.7 |
|  | 25 | 7 | 1.77 ± 0.61 | 49.8 |
|  | 50 | 7 | 1.06 ± 0.38 | 70.1 |
| Physiological saline solution of irinotecan hydrochloride | 12.5 | 7 | 2.82 ± 0.51 | 20.2 |
|  | 25 | 7 | 2.61 ± 0.40 | 26.0 |
|  | 50 | 7 | 2.34 ± 0.17 | 33.7 |
| CPT-11 formulation (Preparation Example 7) | 25 | 11 | 1.70 ± 0.81 | 51.8 |
|  | 50 | 11 | 1.41 ± 0.42 | 60.2 |
| Physiological saline solution of irinotecan hydrochloride | 25 | 11 | 2.40 ± 0.74 | 32.1 |
|  | 50 | 11 | 1.98 ± 0.45 | 44.0 |
| CPT-11 formulation (Preparation Example 7) | 12.5 | 7, 11 | 1.95 ± 0.19 | 44.8 |
|  | 25 | 7, 11 | 1.63 ± 0.39 | 54.0 |
|  | 50 | 7, 11 | 0.65 ± 0.13 | 81.6 |
| Physiological saline solution of irinotecan hydrochloride | 12.5 | 7, 11 | 2.49 ± 0.29 | 29.4 |
|  | 25 | 7, 11 | 2.33 ± 0.62 | 34.1 |
|  | 50 | 7, 11 | 2.08 ± 0.43 | 41.2 |

Example 12

The CPT-11 formulation prepared in Preparation Example 8 as the CPT-11 highly supported formulation of the present invention was tested.

Test Example 15

Antitumor Effect

Human lung cancer cells (QG56) with 2 to 3 mm square were transplanted subcutaneously in an inguinal region of a mouse (BALB/c nude, male, 6 weeks old, CLEA Japan, Inc.) with a needle for transplantation. The CPT-11 formulation prepared in Preparation Example 8 or a physiological saline solution of irinotecan hydrochloride was injected into a caudal vein three times in total which were a point (day 1) at which an estimated volume of a tumor calculated by ½·ab² (a refers to a major axis of a tumor, b refers to a miner axis) approached to around 1 mm³, additional 4 days (day 5), and additional 8 days (day 9), after the transplantation of tumors. Mice without injection of either agent were employed as a control group.

Figure 28:
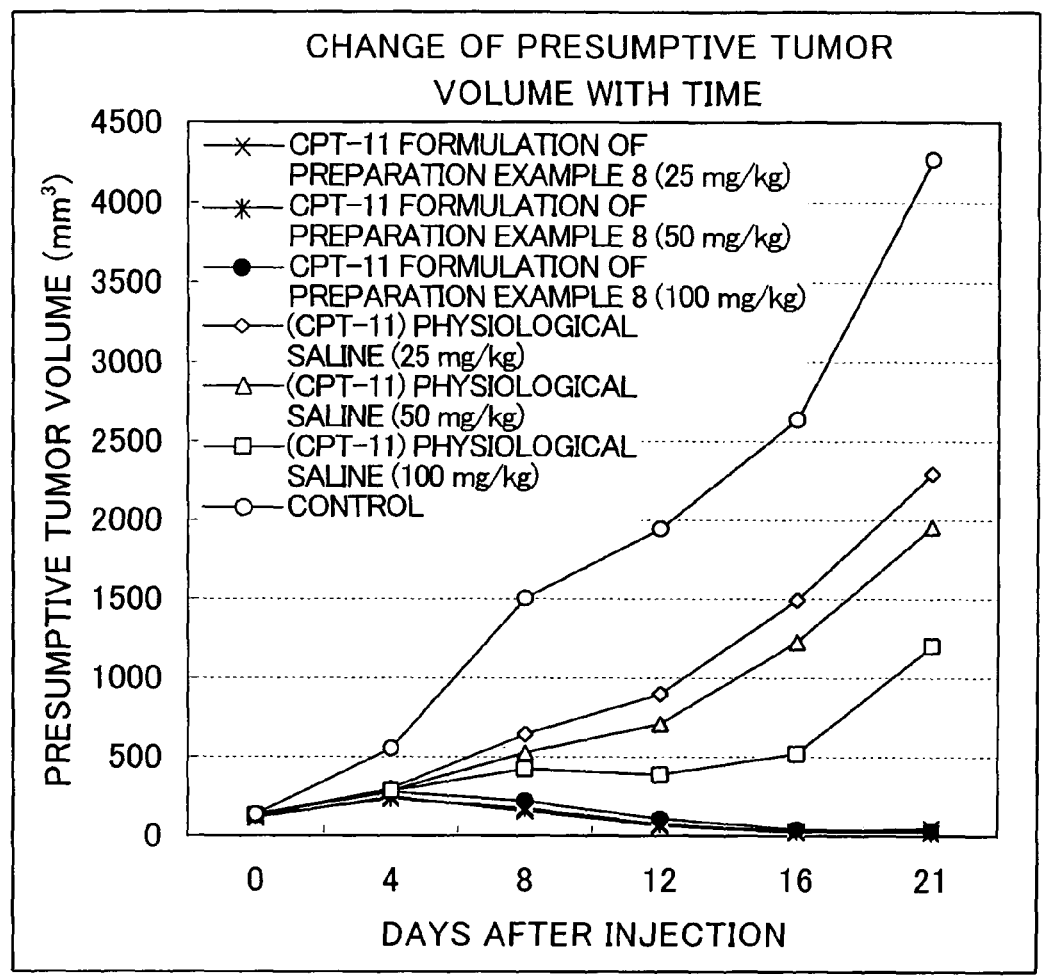
FIG. 28 This is a diagram showing antitumor effect of the CPT-11 preparation by change of presumptive tumor volume with time in Example 12.

The estimated volume of each tumor and a body weight of the mouse were calculated 4, 8, 12, 16, and 21 days after the first injection. The tumors were also removed 21 days after the first injection and a weight of the tumors was measured, to thereby calculate each tumor proliferation inhibition rate, I.R. (%) by the formula as shown in Test Example 6. The results are shown in Table 16, FIG. 28, and FIG. 29.

Figure 29:
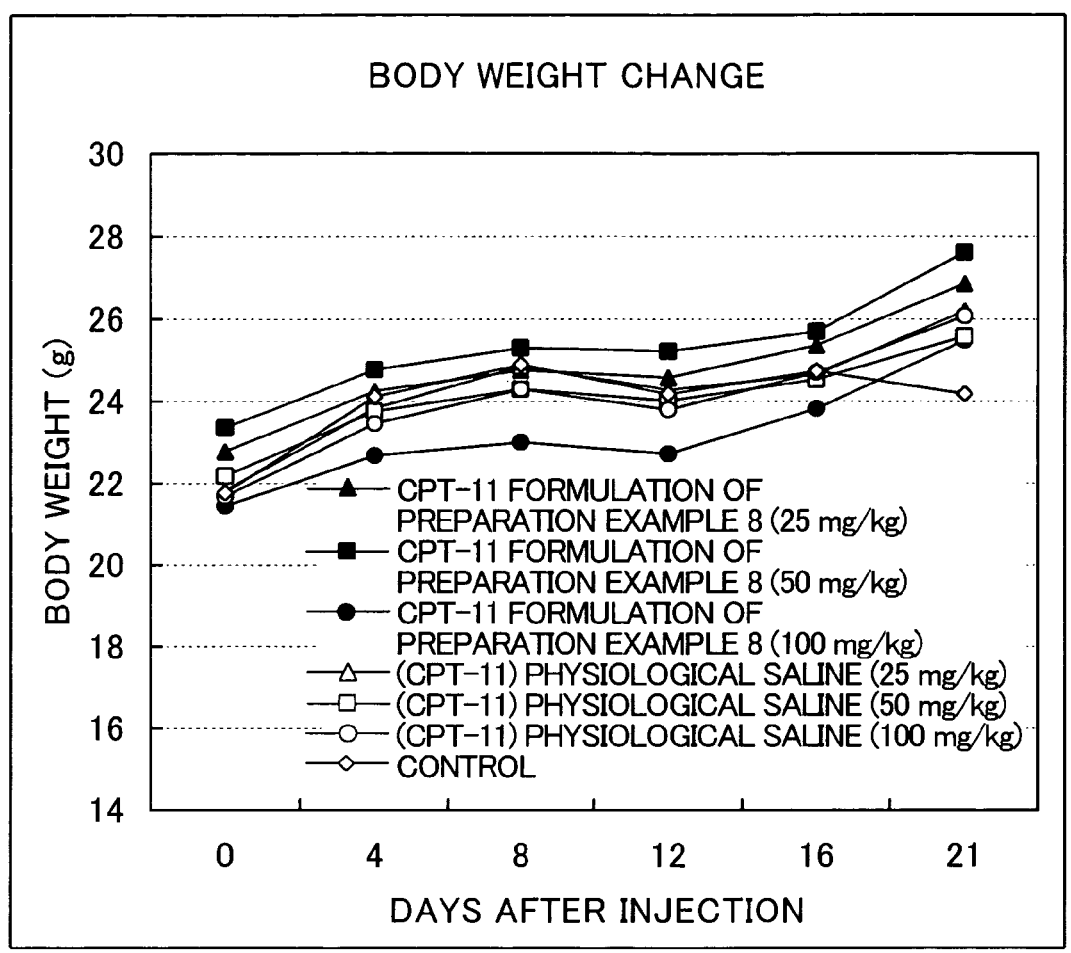
FIG. 29 This is a diagram showing antitumor effect of the CPT-11 preparation by change of a body weight of the mouse in Example 12.

In the human pulmonary carcinoma, the CPT-11 formulation and the physiological saline solution of irinotecan hydrochloride each showed a significant tumor proliferation inhibitory effect compared to the control group. Further, the CPT-11 formulation exhibited a higher antitumor effect than that of the physiological saline solution of irinotecan hydrochloride (Table 16, FIG. 28). Further, either agent didn't affect the body weight of the mouse (FIG. 29).

TABLE 16

| | Dose (mg/kg) | Tumor weight (g, mean ± S.D.) | Inhibition rate (%) |
|---|---|---|---|
| Control group | — | 2.91 ± 0.21 | — |
| CPT-11 formulation | 25 | 0.03 ± 0.02 | 99.0 |
| (Preparation Example 8) | 50 | 0.02 ± 0.00 | 99.3 |
| | 100 | 0.03 ± 0.02 | 99.2 |
| Physiological saline | 25 | 1.88 ± 0.43 | 35.5 |
| solution of irinotecan | 50 | 1.49 ± 0.51 | 48.7 |
| hydrochloride | 100 | 0.95 ± 0.18 | 67.2 |

The invention claimed is:

1. An irinotecan formulation comprising a liposome formed by a membrane of a lipid bilayer containing a phospholipid as a membrane component, wherein only the outer surface of the liposome is modified with a surface-modifying agent containing a polyethylene glycol, in which irinotecan and/or a salt thereof is encapsulated at a concentration of at least 0.1 mol/mol (drug mol/membrane total lipid mol) by an ion gradient between an inner aqueous phase and an outer aqueous phase of the liposome.

2. The irinotecan formulation according to claim 1, wherein the ion gradient is a proton concentration gradient having a pH gradient where a pH value of the inner aqueous phase is lower than a pH value of the outer aqueous phase.

3. The irinotecan formulation according to claim 2, wherein the pH gradient is formed by a concentration gradient of an ammonium ion and/or a concentration gradient of an organic compound having an amino group capable of being protonated.

4. The irinotecan formulation according to claim 1, wherein the liposome further contains a lipid selected from the group consisting of glyceroglycolipids, sphingoglycolipids, sterols and a derivative thereof.

5. The irinotecan formulation according to claim 1, comprising a lipid selected from the group consisting of N-[1-(2,3-dioleyloxy)propyl]-N,N,N-trimethyl ammonium chloride, 1,2-dioleoyl-3-trimethylammonium propane, transfectam, N-(α-trimethyl-ammonioacetyl)didodecyl-D-glutamate chloride, 3,5-dipentadecyloxybenzamidine hydrochloride, TfxTM-50, 2,3-dioleoyloxy-N-[2-sperminecarboxamido)ethyl]-N,N-dimethyl-1-propanaminium trifluoroacetate, didecyldimethylammonium bromide, cholesteryl N-(dimethylaminoethyl) carbamate, and 1,2-dimyristyl oxypropyl-3-dimethyl-hydroxyethyl ammonium bromide.

6. A pharmaceutical composition, comprising the irinotecan formulation according to claim 1.

7. A pharmaceutical composition, comprising the irinotecan formulation according to claim 2.

8. A pharmaceutical composition, comprising the irinotecan formulation according to claim 3.

9. A pharmaceutical composition, comprising the irinotecan formulation according to claim 4.

10. A pharmaceutical composition, comprising the irinotecan formulation according to claim 5.

* * * * *